US012582677B2

(12) United States Patent
Nakano et al.

(10) Patent No.: US 12,582,677 B2
(45) Date of Patent: Mar. 24, 2026

(54) METHODS FOR PRODUCING RETINAL TISSUE AND RETINA-RELATED CELL

(71) Applicants: SUMITOMO CHEMICAL COMPANY, LIMITED, Tokyo (JP); RIKEN, Wako (JP)

(72) Inventors: Tokushige Nakano, Osaka (JP); Satoshi Ando, Osaka (JP); Yoshiki Sasai, Wako (JP); Mototsugu Eiraku, Wako (JP)

(73) Assignees: SUMITOMO CHEMICAL COMPANY, LIMITED, Tokyo (JP); RIKEN, Wako (JP)

( * ) Notice: Subject to any disclaimer, the term of this patent is extended or adjusted under 35 U.S.C. 154(b) by 632 days.

(21) Appl. No.: 17/227,497

(22) Filed: Apr. 12, 2021

(65) Prior Publication Data

US 2021/0228645 A1      Jul. 29, 2021

Related U.S. Application Data

(63) Continuation of application No. 14/360,534, filed as application No. PCT/JP2012/080366 on Nov. 22, 2012, now Pat. No. 10,973,854.

(30) Foreign Application Priority Data

| Nov. 25, 2011 | (JP) | ................................. | 2011-258209 |
| Nov. 25, 2011 | (JP) | ................................. | 2011-258210 |
| Nov. 25, 2011 | (JP) | ................................. | 2011-258211 |
| Nov. 25, 2011 | (JP) | ................................. | 2011-258212 |
| Feb. 29, 2012 | (JP) | ................................. | 2012-043080 |
| Feb. 29, 2012 | (JP) | ................................. | 2012-043081 |
| Feb. 29, 2012 | (JP) | ................................. | 2012-043082 |
| Feb. 29, 2012 | (JP) | ................................. | 2012-043083 |

(51) Int. Cl.

| A61K 35/30 | (2015.01) |
| A61L 27/36 | (2006.01) |
| A61L 27/38 | (2006.01) |
| C12N 5/079 | (2010.01) |
| C12N 5/0793 | (2010.01) |
| G01N 33/50 | (2006.01) |

(52) U.S. Cl.
CPC .......... *A61K 35/30* (2013.01); *A61L 27/3633* (2013.01); *A61L 27/3834* (2013.01); *A61L 27/3895* (2013.01); *C12N 5/062* (2013.01); *C12N 5/0621* (2013.01); *G01N 33/5058* (2013.01); *A61L 2430/16* (2013.01); *C12N 2500/84* (2013.01); *C12N 2500/90* (2013.01); *C12N 2501/16* (2013.01); *C12N 2501/415* (2013.01); *C12N 2501/42* (2013.01); *C12N 2506/02* (2013.01); *C12N 2533/90* (2013.01)

(58) Field of Classification Search
CPC . A61K 35/30; A61L 27/3633; A61L 27/3834; A61L 27/3895; A61L 2430/16; C12N 5/062; C12N 5/0621; C12N 2500/84; C12N 2500/90; C12N 2501/16; C12N 2501/415; C12N 2501/42; C12N 2506/02; C12N 2533/90; G01N 33/5058

See application file for complete search history.

(56) References Cited

U.S. PATENT DOCUMENTS

| 8,354,397 | B2 | 1/2013 | Rubin et al. |
| 8,772,275 | B2 | 7/2014 | Rubin et al. |
| 9,359,592 | B2 | 6/2016 | Park et al. |
| 10,501,724 | B2 | 12/2019 | Nakano et al. |
| 10,973,854 | B2 | 4/2021 | Nakano et al. |
| 11,214,772 | B2 | 1/2022 | Kuwahara et al. |
| 11,371,016 | B2 | 6/2022 | Kuwahara et al. |
| 11,473,056 | B2 | 10/2022 | Nakano et al. |
| 2005/0031599 | A1* | 2/2005 | Kooy .................... A61K 35/44 435/368 |
| 2005/0085519 | A1 | 4/2005 | Rubin et al. |
| 2007/0196919 | A1* | 8/2007 | Reh ...................... C12N 5/0623 435/368 |
| 2008/0044901 | A1 | 2/2008 | Sasai et al. |

(Continued)

FOREIGN PATENT DOCUMENTS

| CN | 101007802 A | 8/2007 |
| CN | 102712900 A | 10/2012 |

(Continued)

OTHER PUBLICATIONS

Mikkola et al. "Superactivation of Pax6-mediated transactivation from paired domain-binding sites by dna-independent recruitment of different homeodomain proteins."J Biol Chem.Feb. 9, 2001;276(6):4109-18. (Year: 2001).*

Meyer et al. "Optic vesicle-like structures derived from human pluripotent stem cells facilitate a customized approach to retinal disease treatment."Stem Cells. Aug. 2011;29(8):1206-18. (Year: 2011).*

De Gendt et al. "Expression of Tubb3, a Beta-Tubulin Isotype, Is Regulated by Androgens in Mouse and Rat Sertoli Cells."Biology of Reproduction, vol. 85, Issue 5, Nov. 1, 2011, pp. 934-945, (Year: 2011).*

(Continued)

*Primary Examiner* — Titilayo Moloye

(74) *Attorney, Agent, or Firm* — Leydig, Voit & Mayer, Ltd.

(57) ABSTRACT

The invention provides a method for producing a retinal tissue by (1) subjecting pluripotent stem cells to floating culture in a serum-free medium containing a substance inhibiting the Wnt signal pathway to form an aggregate of pluripotent stem cells, (2) subjecting the aggregate to floating culture in a serum-free medium containing a basement membrane preparation, and then (3) subjecting the aggregate to floating culture in a serumcontaining medium. The invention also provides a method for producing an optic-cup-like structure, a method for producing a retinal pigment epithelium, and a method for producing a retinal layer-specific neural cell.

12 Claims, 8 Drawing Sheets

(56) References Cited

U.S. PATENT DOCUMENTS

| 2010/0105137 A1 | 4/2010 | Takahashi et al. | |
|---|---|---|---|
| 2011/0081719 A1 | 4/2011 | Gamm et al. | |
| 2011/0223140 A1 | 9/2011 | Park et al. | |
| 2011/0223660 A1 | 9/2011 | Park et al. | |
| 2013/0040330 A1* | 2/2013 | Sasai ................... | C12N 5/0623 |
| | | | 435/325 |
| 2013/0190350 A1 | 7/2013 | Rubin et al. | |
| 2014/0341864 A1 | 11/2014 | Nakano et al. | |
| 2016/0251616 A1 | 9/2016 | Nakano et al. | |
| 2016/0264936 A1 | 9/2016 | Nakano et al. | |
| 2017/0191033 A1 | 7/2017 | Azuma et al. | |
| 2017/0313981 A1 | 11/2017 | Kuwahara et al. | |
| 2019/0127690 A1 | 5/2019 | Kuwahara et al. | |
| 2020/0102535 A1 | 4/2020 | Nakano et al. | |
| 2022/0119764 A1 | 4/2022 | Kuwahara et al. | |
| 2022/0364054 A1 | 11/2022 | Nakano et al. | |

FOREIGN PATENT DOCUMENTS

| CN | 105683366 A | 6/2016 |
|---|---|---|
| CN | 107002040 A | 8/2017 |
| CN | 109312306 A | 2/2019 |
| WO | WO 2005/123902 A1 | 12/2005 |
| WO | WO 2008/087917 A1 | 7/2008 |
| WO | WO 2008/129554 A1 | 10/2008 |
| WO | WO 2009/051671 A1 | 4/2009 |
| WO | WO 2011/055855 A1 | 5/2011 |

OTHER PUBLICATIONS

Roberts et al. "Retinoid X Receptor γ Is Necessary to Establish the S-opsin Gradient in Cone Photoreceptors of the Developing Mouse Retina." Investigative Ophthalmology & Visual Science Aug. 2005, vol. 46, 2897-2904. (Year: 2005).*

Lamba et al. "Microarray Characterization of Human Embryonic Stem Cell-Derived Retinal Cultures." Investigative Ophthalmology & Visual Science Jun. 2011, vol. 52, 4897-4906. (Year: 2011).*

"Merriam-Webster."Orderly Definition and Meaning. https://www.merriam-webster.com/dictionary/orderly. Webstite acessed Jan. 14, 2025. (Year: 2025).*

U.S. Appl. No. 14/360,534, filed May 23, 2014.

Bayramov et al., "Novel functions of Noggin proteins: inhibition of Activin/Nodal and Wnt signaling," Development, 138(24): 5345-5356 (2011).

Eiraku et al., "Self-organizing optic-cup morphogenesis in three-dimensional culture," Nature, 472(7341): 51-56 (Apr. 7, 2011).

Eiraku et al., "Mouse embryonic stem cell culture for generation of three-dimensional retinal and cortical tissues," Nature Protocols, 7(1): 69-79 (2012) [published online Dec. 15, 2011].

Hagos et al., "Time-dependent patterning of the mesoderm and endoderm by Nodal signals in zebrafish," BMC Dev. Biol., 7: 22 (2007).

Idelson et al., "Directed Differentiation of Human Embryonic Stem Cells into Functional Retinal Pigment Epithelium Cells," Cell Stem Cell, 5(4): 396-408 (Oct. 2, 2009).

Ikeda et al., "Generation of Rx+/Pax6+ neural retinal precursors from embryonic stem cells," PNAS, 102(32): 11331-11336 (2005).

Lamba et al., "Efficient generation of retinal progenitor cells from human embryonic stem cells," PNAS, 103(34): 12769-12774 (2006).

Mellough et al., "Efficient Stage-Specific Differentiation of Human Pluripotent Stem Cells Toward Retinal Photoreceptor Cells", Stem Cells, 30: 673-686 (2012).

Meyer et al., "Modeling early retinal development with human embryonic and induced pluripotent stem cells" PNAS, 106(39): 16698-16703 (2009).

Nakano et al., "Self-Formation of Optic Cups and Storable Stratified Neural Retina from Human ESCs," Cell Stem Cell, 10(6): 771-785 (Jun. 14, 2012).

Osakada et al., "Toward the generation of rod and cone photoreceptors from mouse, monkey and human embryonic stem cells," Nature Biotechnology, 26(2): 215-224 (2008).

Osakada et al., "Stepwise differentiation of pluripotent stem cells into retinal cells" Nature Protocols, 4(6): 811-824 (2009).

Phillips et al., "Blood-derived Human IPS Cells Generate Optic Vesicle-like Structures with the Capacity to Form Retinal Laminae and Develop Synapses," Invest Ophthalmol. Vis. Sci., Manuscript IOVS.11-9313 (Mar. 12, 2012).

Riazifar et al., "Chemically-induced specification of retinal ganglion cells from human embryonic and induced pluripotent stem cells," Mitochondrion, 13(6): 903, abstract 16 (2014).

Schouwey et al., "RBP-Jκ-dependent Notch signaling enhances retinal pigment epithelial cell proliferation in transgenic mice," Oncogene, 30(3): 313-322 (2011).

Shen, "Nodal signaling: developmental roles and regulation," Development, 134(6): 1023-1034 (2007).

Smith et al., "Inhibition of Activin/Nodal signaling promotes specification of human embryonic stem cells into neuroectoderm," Dev. Biol., 313(1): 107-117 (2008).

European Patent Office, Supplementary Partial European Search Report in European Patent Application No. 12851901 (Jun. 18, 2015).

European Patent Office, Supplementary European Search Report in European Patent Application No. 12851901 (Oct. 2, 2015).

Japanese Patent Office, International Search Report in International Patent Application PCT/JP2012/080366 (Feb. 12, 2013).

Chen et al., "Research Progress of the Differentiation of Stem Cells into Retinal Photoreceptor Cells Induced by Small Molecular Compounds," Progress in Modern Biomedicine, 17(14): 2797-2800 (2017).

Liu et al., "Clinical Anatomy of Ophthalmology," Shandong Science and Technology Press, 1: 28-29 (2009).

Zhang et al., "Progress and Challenges of the Directed Differentiation of Pluripotent Stem Cells into Photoreceptor Cells and Visual Repair," China Basic Science, 19(2): 22-26 (2017).

China National Intellectual Property Administration, Office Action in Chinese Patent Application No. 2021111105844 (Feb. 27, 2024).

* cited by examiner without Wnt inhibitor
with Matrigel with Nodal inhibitor
(SB431542)
(without Wnt inhibitor)
with Matrigel with Wnt inhibitor
with Matrigel

Figure 2:
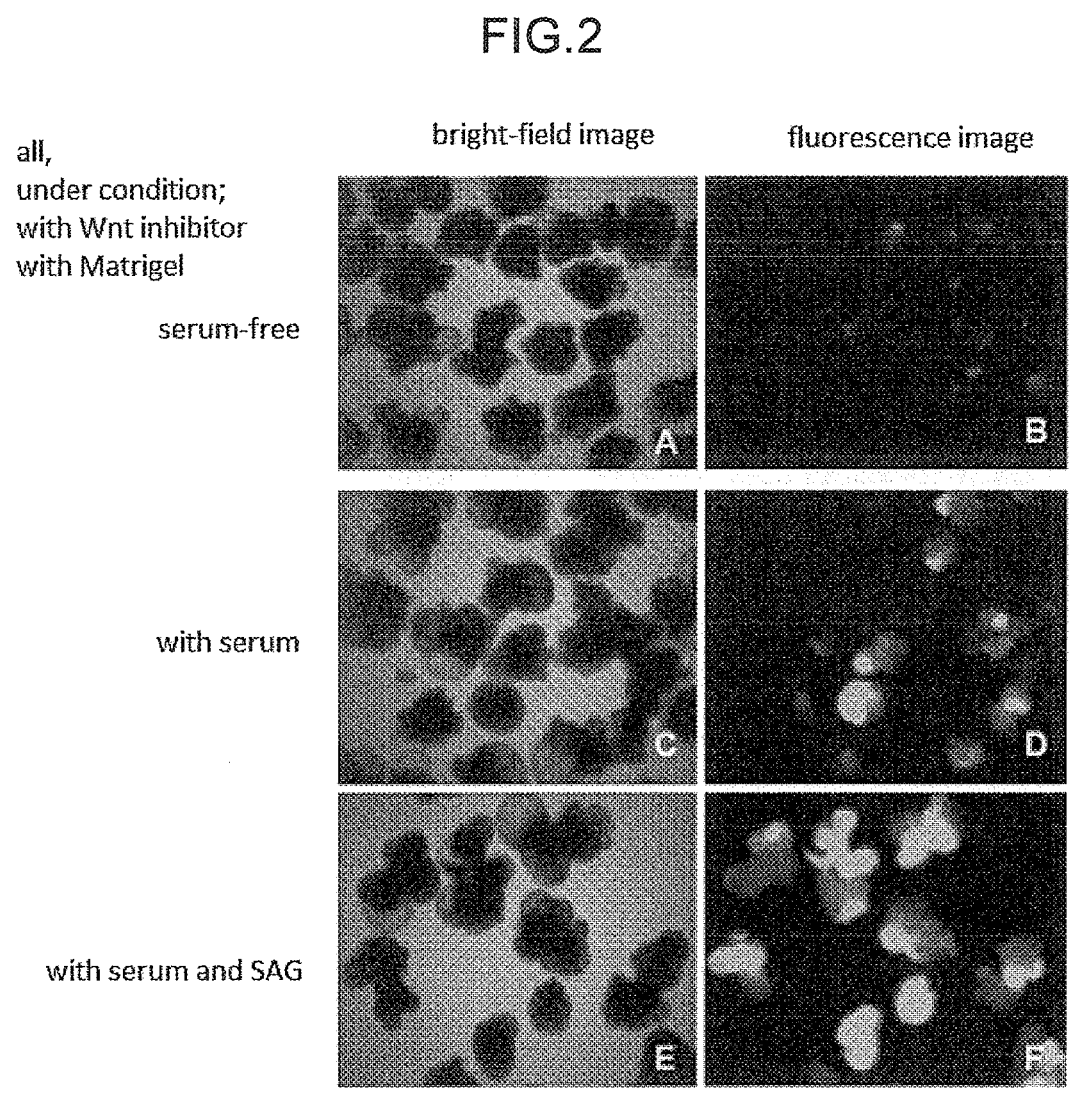

FIG.2 all,
under condition;
with Wnt inhibitor
with Matrigel bright-field image        fluorescence image serum-free with serum with serum and SAG (d29-d41) Control

DAPT after freeze-thawing
DAPT treatment of retinal tissue

METHODS FOR PRODUCING RETINAL TISSUE AND RETINA-RELATED CELL

CROSS-REFERENCE TO RELATED APPLICATIONS

This patent application is a continuation of copending U.S. patent application Ser. No. 14/360,534, filed on May 23, 2014, and issued on Apr. 13, 2021, as U.S. Pat. No. 10,973,854, which is the U.S. national phase of International Patent Application No. PCT/JP2012/080366, filed Nov. 22, 2012, which claims the benefit of Japanese Patent Application No. 2011-258212, filed on Nov. 25, 2011, Japanese Patent Application No. 2011-258211, filed on Nov. 25, 2011, Japanese Patent Application No. 2011-258210, filed on Nov. 25, 2011, Japanese Patent Application No. 2011-258209, filed on Nov. 25, 2011, Japanese Patent Application No. 2012-043083, filed on Feb. 29, 2012, Japanese Patent Application No. 2012-043082, filed on Feb. 29, 2012, Japanese Patent Application No. 2012-043081, filed on Feb. 29, 2012, and Japanese Patent Application No. 2012-043080, filed on Feb. 29, 2012, which are incorporated by reference in their entireties herein.

TECHNICAL FIELD

The present invention relates to a method for producing a retinal tissue, and retina-related cells such as retinal layer-specific nerve cell, retinal pigment epithelium, and so on.

BACKGROUND ART

The central nervous system tissues such as the brain and retina have low regenerative capacity and damaged tissues scarcely recover spontaneously. Therefore, regenerative medicine that transplants cells differentiated from pluripotent stem cells for the treatment is expected to be the last card for overcoming intractable diseases. Furthermore, human-derived cells obtained by differentiation from pluripotent stem cells are considered to be able to accurately evaluate the effects of chemical substances on human, and the research and development toward application to toxicity evaluation of compounds and drug discovery are underway.

Retina is an important sensory tissue that receives light, converts it to electrical signals and, after information processing, conveys the information via axons to the visual center of the brain. Retina is largely made of two inside and outside epithelial tissues superimposed on top of each other. The inside is a neural retina that receives light and processes information, and contains more than one type of cell such as photoreceptor. The outside is a retinal pigment epithelium which is a monolayer cell sheet that supports the survival and function of the photoreceptors.

There have been known reports on the production of retinal layer-specific nerve cells constituting the neural retina (photoreceptors, horizontal cells, amacrine cells, ganglion cells and so on) from pluripotent stem cells (patent document 1). Furthermore, as a method for producing a three-dimensional retinal tissue from pluripotent stem cells, it is described that retinal progenitor tissue, optic-cup-like structure and multi-layer neural retinal tissue can be produced in vitro by forming homogeneous pluripotent stem cell aggregates in a serum-free medium and subjecting them to floating culture in the presence of a basement membrane preparation (non-patent document 1 and patent document 2).

On the other hand, a report on the production of retinal pigment epithelia by using pluripotent stem cells is also known (non-patent document 2). However, there is no report on the production of retinal pigment epithelia with high efficiency.

DOCUMENT LIST

Patent Documents patent document 1: WO 2008/087917
patent document 2: WO 2011/055855

Non-Patent Documents non-patent document 1: Mototsugu Eiraku, Nozomu Takata, Hiroki Ishibashi, Masako Kawada, Eriko Sakakura, Satoru Okuda, Kiyotoshi Sekiguchi, Taiji Adachi & Yoshiki Sasai (2011) Self-organizing optic-cup morphogenesis in three-dimensional culture. Nature Volume: 472, Pages: 51-56
non-patent document 2: Maria Idelson, Ruslana Alper, Alexey Obolensky, Etti Ben-Shushan, Itzhak Hemo, Nurit Yachimovich-Cohen, Hanita Khaner, Yoav Smith, Ofer Wiser, Michal Gropp, Malkiel A. Cohen, Sharona Even-Ram, Yael Berman-Zaken, Limor Matzrafi, Gideon Rechavi, Eyal Banin, and Benjamin Reubinoff (2009) Directed Differentiation of HumanEmbryonic Stem Cells into Functional Retinal Pigment Epithelium Cells. Cell Stem Cell 5, 396-408

SUMMARY OF THE INVENTION

Problems to be Solved by the Invention

A method for producing retinal tissue, optic-cup-like structure and retinal layer-specific nerve cell, and retinal pigment epithelium with higher efficiency has been demanded.

Means of Solving the Problems

The present inventors have conducted intensive studies in view of such situation and arrived at the present invention.

Accordingly, the present invention is as follows. [1]A method for producing a retinal tissue, comprising the following steps (1) to (3):

(1) a first step of subjecting pluripotent stem cells to floating culture in a serum-free medium containing a substance inhibiting the Wnt signal pathway to form an aggregate of pluripotent stem cells, (2) a second step of subjecting the aggregate formed in the first step to floating culture in a serum-free medium containing a basement membrane preparation, and (3) a third step of subjecting the aggregate cultured in the second step to floating culture in a serum-containing medium.

[2]A method for producing an optic-cup-like structure, comprising a step of subjecting the retinal tissue obtained by the method of the aforementioned [1] to floating culture in a serum-free medium or serum-containing medium each containing a substance acting on the Sonic hedgehog (hereinafter, sometimes referred to as "Shh") signal pathway and a substance acting on the Wnt signal pathway.

[3]A method for producing a retinal pigment epithelium, comprising a step of subjecting the retinal tissue obtained by the method of the aforementioned [1] to floating culture in a serum-free medium or serum-containing medium each containing a substance acting on the Wnt signal pathway (wherein the aforementioned serum-free medium and serum-containing medium are free of a substance acting on the Sonic hedgehog (hereinafter, sometimes referred to as "Shh") signal pathway).

[4] The method of the aforementioned [3], wherein the aforementioned serum-free medium or serum-containing medium containing a substance acting on the Wnt signal pathway further comprises a substance acting on the Activin signal pathway.

[5] The method of any of the aforementioned [1] to [4], wherein the aforementioned pluripotent stem cells are primate pluripotent stem cells.

[6] The method of any of the aforementioned [1] to [4], wherein the aforementioned pluripotent stem cells are human pluripotent stem cells.

[7] The method of any of the aforementioned [1] to [6], wherein the aforementioned basement membrane preparation is at least one extracellular matrix molecule selected from the group consisting of laminin, type IV collagen, heparan sulfate proteoglycan and entactin.

[8] The method of any of the aforementioned [1] to [7], wherein the aforementioned first step to the third step are performed in the presence of Knockout serum replacement (hereinafter, sometimes referred to as "KSR").

[9] A method for producing a retinal layer-specific neural cell, comprising bringing a retinal progenitor cell contained in a retinal tissue derived from a primate pluripotent stem cell into contact with a substance inhibiting the Notch signal pathway.

[10] The method of the aforementioned [9], wherein the aforementioned substance inhibiting the Notch signal pathway is a gamma secretase activity inhibitory substance.

[11] The method of the aforementioned [9] or [10], wherein the aforementioned substance inhibiting the Notch signal pathway is N-[N-(3,5-difluorophenacetyl)-L-alanyl]-S-phenylglycine t-butyl ester (hereinafter, sometimes referred to as "DAPT").

[12] The method of any of the aforementioned [9] to [11], wherein the aforementioned primate is human.

[13] The method of any of the aforementioned [9] to [12], wherein the retinal layer-specific neural cell is a photoreceptor

[14] The method of any of the aforementioned [9] to [12], wherein the retinal layer-specific neural cell is a ganglion cell.

[15] The method of any of the aforementioned [9] to [14], wherein the retinal progenitor cell contained in the retinal tissue derived from a primate pluripotent stem cell is a retinal progenitor cell contained in a retinal tissue produced by the following steps:

(1) a first step of subjecting primate pluripotent stem cells to floating culture in a serum-free medium containing a substance inhibiting the Wnt signal pathway to form an aggregate of primate pluripotent stem cells, (2) a second step of subjecting the aggregate formed in the first step to floating culture in a serum-free medium containing a basement membrane preparation, (3) a third step of subjecting the aggregate cultured in the second step to floating culture in a serum-containing medium, (4) a fourth step of subjecting the aggregate cultured in the third step to floating culture in a serum-free medium or serum-containing medium each containing a substance acting on the Sonic hedgehog (hereinafter, sometimes referred to as "Shh") signal pathway and a substance acting on the Wnt signal pathway, to form an optic-cup-like structure, and (5) a step of subjecting the optic-cup-like structure formed in the fourth step to floating culture.

[16] A reagent for evaluating toxicity or drug efficacy, comprising a retinal tissue, an optic-cup-like structure, a retinal pigment epithelium or a retinal layer-specific neural cell produced by the method of any of the aforementioned [1] to [15].

[17] A method for evaluating toxicity or drug efficacy of a test substance, comprising bringing a retinal tissue, an optic-cup-like structure, a retinal pigment epithelium or a retinal layer-specific neural cell produced by the method of any of the aforementioned [1] to [15] into contact with the test substance, and examining the influence of the substance on the tissue, structure or cell.

[18] A therapeutic agent for a disease due to a disorder of a retinal tissue, comprising a retinal tissue, an optic-cup-like structure, a retinal pigment epithelium or a retinal layer-specific neural cell produced by the method of any of the aforementioned [1] to [15].

[19] A method for treating a disease due to a disorder of a retinal tissue, comprising transplanting an effective amount of a retinal tissue, an optic-cup-like structure, a retinal pigment epithelium or a retinal layer-specific neural cell produced by the method of any of the aforementioned [1] to [15] to a target in need of the transplantation.

[20] A retinal tissue, an optic-cup-like structure, a retinal pigment epithelium or a retinal layer-specific nerve cell produced by the method of any of the aforementioned [1] to [15] for use in the treatment of a disease due to a disorder of a retinal tissue.

Effect of the Invention

According to the present invention, a retinal tissue, optic-cup-like structure, retinal layer-specific nerve cell or retinal pigment epithelium can be produced at high efficiency. Accordingly, in view of efficient provision of a retinal tissue, optic-cup-like structure, retinal layer-specific nerve cell or retinal pigment epithelium for the purpose of toxicity or drug efficacy evaluation of a chemical substance, etc., a transplantation treatment and so on, the present invention is highly useful.

BRIEF DESCRIPTION OF THE DRAWINGS

FIG. 2 is a view that shows a bright-field image (A) and a fluorescence image (B) of aggregates on day 18 from the start of the floating culture, which were produced by floating culture of human pluripotent stem cells by adding a substance inhibiting the Wnt signal pathway, floating culture thereof in the presence of Matrigel and further floating culture thereof in the absence of fetal calf serum, a bright-field image (C) and a fluorescence image (D) of aggregates on day 18 from the start of the floating culture, which were produced by floating culture of human pluripotent stem cells by adding a substance inhibiting the Wnt signal pathway, floating culture thereof in the presence of Matrigel and further floating culture thereof in the presence of fetal calf serum, and a bright-field image (E) and a fluorescence image (F) of aggregates on day 18 from the start of the floating culture, which were produced by floating culture of human pluripotent stem cells by adding a substance inhibiting the Wnt signal pathway, floating culture thereof in the presence of Matrigel and further floating culture thereof in the presence of fetal calf serum and a substance acting on the Sonic hedgehog (hereinafter, sometimes referred to as "Shh") signal pathway.

Figure 9:
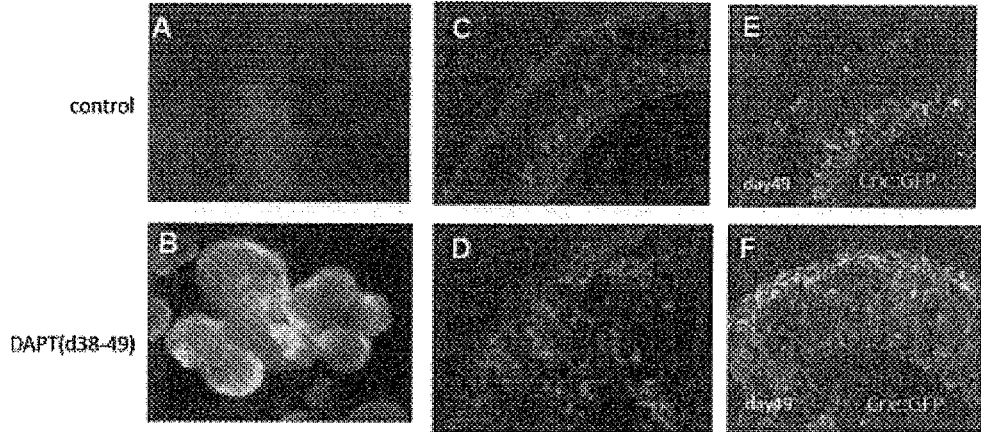

FIG. 9 is a view that shows a fluorescence microscope (A) in the case of floating culture, until day 49 from the start of the floating culture under the conditions without addition of 10 μM DAPT, a fluorescence microscope (B) in the case of floating culture until day 49 from the start of the floating culture under the conditions with addition of DAPT, photograph of a frozen section immunostained with an anti-Recoverin antibody (C) or with an anti-Brn3 antibody (E) in the case of floating culture until day 49 from the start of the floating culture under the conditions without addition of 10 μM DAPT, and photograph of frozen section immunostained with an anti-Recoverin antibody (D) or with an anti-Brn3 antibody (F) in the case of floating culture until day 49 from the start of the floating culture under the conditions with addition of DAPT, of a Crx::GFP knock-in human ES cell-derived retinal tissue on day 38 from the start of the floating culture after freeze-thawing the retinal tissue on day 33 from the start of the floating culture.

Figure 10:
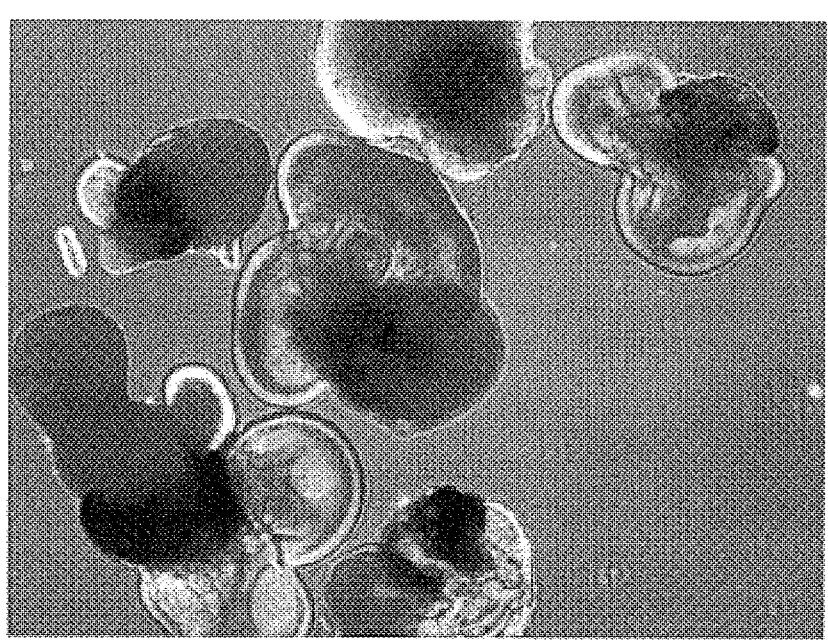

FIG. 10 is a view that shows a bright-field of an aggregate produced by floating culture in a serum-free medium containing a substance inhibiting the Wnt signal pathway to form an aggregate, floating culture of the formed aggregate in a serum-free medium in the presence of a basement membrane preparation, culturing the cultured aggregate in a medium containing a serum, and culturing the cultured aggregate in a medium containing a substance acting on the Wnt signal pathway.

Figure 11:
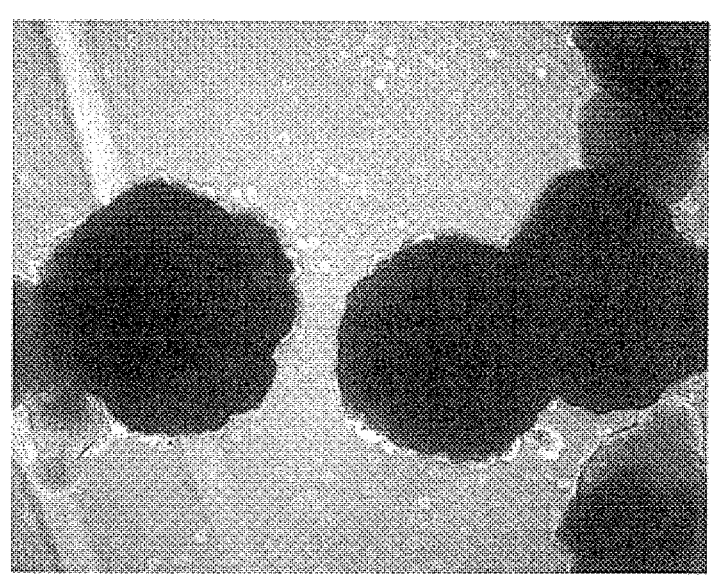

FIG. 11 is a view that shows a bright-field of an aggregate produced by floating culture in a serum-free medium containing a substance inhibiting the Wnt signal pathway to form an aggregate, floating culture of the formed aggregate in a serum-free medium in the presence of a basement membrane preparation, culturing the cultured aggregate in a medium containing a serum, and culturing the cultured aggregate in a medium containing a substance acting on the Wnt signal pathway and a substance acting on the Activin A pathway.

MODE(S) FOR CARRYING OUT THE INVENTION

Mode(s) for carrying out the present invention is explained in detail below.

In the present invention, the "transformant" means the entirety or a part of the living matter such as cell produced by transformation. Examples of the transformant include prokaryotic cell, yeast, animal cell, plant cell, insect cell and so on. Depending on the target, the transformant is also sometimes called transformed cell, transformed tissue, transformed host and so on. The cell used in the present invention may also be a transformant.

Examples of the prokaryotic cell used for genetically-engineered technique in the present invention include prokaryotic cells belonging to the genus *Escherichia*, the genus *Serratia*, the genus *Bacillus*, the genus *Brevibacterium*, the genus *Corynebacterium*, the genus *Microbacterium*, the genus *Pseudomonas* and so on, such as *Escherichia* XL1-Blue, *Escherichia* XL2-Blue, and *Escherichia* DH1. These cells are specifically described in, for example, "Molecular Cloning (3rd edition)" by Sambrook, J and Russell, D. W., Appendix 3 (Volume 3), Vectors and Bacterial strains. A3.2 (Cold Spring Harbor USA 2001).

The "vector" in the present invention means a vector capable of transferring a desired polynucleotide sequence into an object cell. Examples of such vector include those capable of autonomously replicating in a host cell such as prokaryotic cell, yeast, animal cell, plant cell, insect cell, animal individual and plant individual, or capable of being incorporated into a chromosome, and containing a promoter at a position suitable for polynucleotide transcription.

Of such vectors, a vector suitable for cloning is sometimes indicated as a "cloning vector". Such cloning vector generally has multiple cloning sites containing a plurality of restriction enzyme sites. At present, there are many vectors usable for gene cloning in the pertinent field, and they are sold by distributors with different names since they are slightly different (e.g., kind and sequence of restriction enzymes at multi cloning sites). For example, representative ones are described (distributors are also described) in "Molecular Cloning (3rd edition)" by Sambrook, J and Russell, D. W., Appendix 3 (Volume 3), Vectors and Bacterial strains. A3.2 (Cold Spring Harbor USA, 2001), and those of ordinary skill in the art can use them as appropriate according to the object.

The "vector" in the present invention also includes "expression vector", "reporter vector", and "recombinant vector". The "expression vector" means a nucleic acid sequence wherein various regulatory elements in addition to a structural gene and a promoter that regulates the expression thereof are linked in such a manner that they can be operable in the host cell. Examples of the "regulatory element" include terminator, selection marker such as a drug resistance gene, and one containing an enhancer. It is well known to those of ordinary skill in the art that the type of an expression vector of living matter (e.g., animal) and the kind of the regulatory element to be used may vary depending on the host cell.

Examples of the "recombinant vector" in the present invention include (a) lambda FIX vector (phage vector) for screening for genomic library, (b) lambda ZAP vector (phage vector) for screening for cDNA, and (c) pBluescript II SK+/−, pGEM, and pCR2.1 vector (plasmid vector) for cloning of genomic DNA. Examples of the "expression vector" include pSV2/neo vector, pcDNA vector, pUC18 vector, pUC19 vector, pRc/RSV vector, pLenti6/V5-Dest vector, pAd/CMV/V5-DEST vector, pDON-AI-2/neo vector, and pMEI-5/neo vector (plasmid vector) and so on. Examples of the "reporter vector" include pGL2 vector, pGL3 vector, pGL4.10 vector, pGL4.11 vector, pGL4.12 vector, pGL4.70 vector, pGL4.71 vector, pGL4.72 vector, pSLG vector, pSLO vector, pSLR vector, pEGFP vector, pAcGFP vector, pDsRed vector and so on. These vectors can be utilized as appropriate by reference to the aforementioned Molecular Cloning reference.

As a technique for introducing a nucleic acid molecule into a cell in the present invention, for example, transformation, transduction, transfection and so on can be mentioned. As such introduction technique, for example, the methods described in Ausubel F. A. et al. ed. (1988), Current Protocols in Molecular Biology, Wiley, New York, NY; Sambrook J. et al. (1987), Molecular Cloning: A Laboratory Manual, 2nd Ed. and 3rd Ed.; Cold Spring Harbor Labora-tory Press, Cold Spring Harbor, NY; extra issue, Experimental Medicine "transgene & expression analysis experiment method" YODOSHA CO., LTD., 1997, and so on can be specifically mentioned. As the technique for confirming intracellular introduction of a gene, for example, Northern blot analysis, Western blot analysis and other well-known conventional techniques and so on can be mentioned.

In the present invention, the "stem cell" refers to a cell that maintains the same differentiation capacity even after cell division, and a tissue thereof can be regenerate when the tissue is injured. Here, the stem cell may be an embryonic stem cell (ES cell) or a tissue stem cell (also called tissular stem cell, tissue-specific stem cell or somatic stem cell), or an artificial pluripotent stem cell (iPS cell: induced pluripotent stem cell) but is not limited thereto. As appreciated from the fact that the above-mentioned stem cell-derived tissue cell can regenerate a tissue, it is known that the stem cell can differentiate into a normal cell close to one in a living body.

Stem cells are available from given organizations, or a commercially available product can also be purchased. For example, human embryonic stem cells, KhES-1, KhES-2 and KhES-3, are available from Kyoto University's Institute for Frontier Medical Sciences. EB5 cell, which is a mouse embryonic stem cell, is available from RIKEN, and D3 cell line is available from ATCC.

Stem cells can be maintained by culturing according to a method known per se. For example, stem cells can be maintained by feeder cell-free culture supplemented with fetal calf serum (FCS), Knockout Serum Replacement (KSR), and LIF.

In the present invention, the "pluripotent stem cell" refers to a stem cell that can be cultured in vitro and has an ability to differentiate into any cell (triploblast (ectoderm, mesoderm, endoderm)-derived tissue) constituting a living body except for placenta (differentiation pluripotency), including an embryonic stem cell (ES cell). The "pluripotent stem cell" is obtained from fertilized egg, clone embryo, reproductive stem cell, and stem cell in a tissue. It also includes a cell having artificial differentiation pluripotency similar to that of embryonic stem cells, after introducing several kinds of genes into a somatic cell (also called artificial pluripotent stem cell). Pluripotent stem cell can be produced by a method known per se. Examples of the production method include the methods described in Cell 131(5) pp. 861-872, Cell 126(4) pp. 663-676 and so on.

In the present invention, the "embryonic stem cell (ES cell)" refers to a stem cell having a self replication ability and multipotency (i.e., "pluripotency"), which is a pluripotent stem cell derived from an early embryo. Embryonic stem cell was first established in 1981, and has also been applied to the generation of knockout mouse since 1989. In 1998, a human embryonic stem cell was established, which is also being utilized for regenerative medicine.

In the present invention, the "artificial pluripotent stem cell" refers to a cell induced to have multipotency by directly reprogramming a differentiated cell such as fibroblast etc. by the expression of several kinds of genes such as Oct3/4, Sox2, Klf4, and Myc, which was established by Yamanaka et al. in mouse cell in 2006 (Takahashi K, Yamanaka S. Cell. 2006, 126(4), p 663-676). In 2007, it was also established in human fibroblast, and has multipotency similar to that of embryonic stem cells (Takahashi K, Tanabe K, Ohnuki M, Narita M, Ichisaka T, Tomoda K, Yamanaka S. Cell. 2007, 131(5), p 861-872.; Yu J, Vodyanik M A, Smuga-Otto K, Antosiewicz-Bourget J, Frane J L, Tian S, Nie J, Jonsdottir G A, Ruotti V, Stewart R, Slukvin II, Thomson J A., Science. 2007, 318(5858), p 1917-1920.; Nakagawa M, Koyanagi M, Tanabe K, Takahashi K, Ichisaka T, Aoi T, Okita K, Mochiduki Y, Takizawa N, Yamanaka S. Nat Biotechnol., 2008, 26(1), p 101-106).

Is A genetically-modified pluripotent stem cell can be produced, for example, using a homologous recombination technique. Examples of the gene on the chromosome, which is to be modified for the production of a modified pluripotent stem cell, include a histocompatibility antigen gene, a gene related to a disease due to a disorder of nerve system cell and so on. A target gene on the chromosome can be modified by the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Bio Manual series 8, gene targeting, Production of mutant mouse by using ES cells, YODOSHA CO., LTD. (1995) and so on.

To be specific, for example, the genomic gene of a target gene to be modified (e.g., histocompatibility antigen gene, disease-related gene and so on) is isolated, and a target vector used for homologous recombination of the target gene is produced using the isolated genomic gene. The produced target vector is introduced into stem cells, and cells showing homologous recombination between the target gene and the target vector are selected, whereby stem cells having modified gene on the chromosome can be produced.

As a method for isolating the genomic gene of the target gene, known methods described in Molecular Cloning, A Laboratory Manual, Second Edition, Cold Spring Harbor Laboratory Press (1989), Current Protocols in Molecular Biology, John Wiley & Sons (1987-1997) and so on can be mentioned. Moreover, the genomic gene of the target gene can be isolated using genomic DNA library screening system (manufactured by Genome Systems), Universal Genome Walker Kits (manufactured by CLONTECH) and so on.

A target vector used for homologous recombination of the target gene can be produced, and a homologous recombinant can be efficiently selected according to the methods described in Gene Targeting, A Practical Approach, IRL Press at Oxford University Press (1993); Bio Manual series 8, gene targeting, Production of mutant mouse by using ES cells, YODOSHA CO., LTD. (1995) and so on. The target vector may be any of replacement type and insertion type, and the selection method may be positive selection, promoter selection, negative selection, polyA selection and so on.

As a method for selecting an object homologous recombinant from the selected cell lines, Southern hybridization method, PCR method and so on for genomic DNA can be mentioned.

In the present invention, the "tissue" refers to a structure of a cell population, which has a conformation wherein more than one type of cell different in the shape and property are sterically configured in a given pattern.

In the present invention, the "retinal tissue" means a retinal tissue wherein at least two or more types of cells such as photoreceptors, horizontal cells, bipolar cells, amacrin cells, retinal ganglion cells, their precursor cells or retinal progenitor cells thereof, which constitute respective retinal layers in living retina, are sterically arranged in layers. With regard to each cell, which cell constitutes which retinal layer can be confirmed by a known method, for example, the expression of a cell marker.

Examples of the retina cell marker include, but are not limited to, Rax (progenitor cell of retina), PAX6 (progenitor cell), nestin (expressed in progenitor cell of hypothalamus neuron but not expressed in retinal progenitor cell), Sox1 (expressed in hypothalamus neuroepithelium but not expressed in retina), Crx (precursor cell of photoreceptor), and so on. In particular, examples of the marker of the above-mentioned retinal layer-specific neuron include, but are not limited to, Chx10 (bipolar cell), L7 (bipolar cell), Tuj1 (ganglion cell), Brn3 (ganglion cell), Calretinin (amacrine cell), Calbindin (horizontal cell), Rhodopsin (photoreceptor), Recoverin (photoreceptor), RPE65 (pigment epithelium), Mitf (pigment epithelium) Nr1 (rod cell), Rxr-gamma (cone cell) and so on.

In the present invention, the "optic-cup-like structure" refers to a structure having a shape similar to that of the optic cup in the development process of embryo. In the development process of embryo, the primordium of retina is developed from the side face of diencephalon, and formed like a pouch protruding from the diencephalon. The pouch-like epithelial structure is called an optic vesicle. The outermost part of the optic vesicle (to be the neural retina in the future) gradually invaginates toward the inside of the optic vesicle, and forms an optic cup which is a cup-like tissue composed of two inside and outside layers of epithelium. The optic cup thereafter grows large and forms the retina with a retinal tissue. Whether it is an optic-cup-like structure can be confirmed by those of ordinary skill in the art through observation with a microscope, a magnifying glass and so on.

The optic-cup-like structure to be produced in the present invention shows not only a morphologically optic cup-like protrusion but also highly frequent expression of Rax, which is a retinal progenitor cell marker, in the cells constituting the optic-cup-like structure. In addition, the outer layer of the optic-cup-like structure also shows a layer of retinal pigment epithelia expressing Mitf, and the inner layer shows cells constituting retinal tissues, such as retinal progenitor cells expressing Chx10. Such optic-cup-like structure closely resembles the structure of optic cup tissues in the development of a living body.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

The "retinal layer-specific neural cell" in the present invention means a neural cell constituting a retinal layer and specific to the retinal layer.

The "retinal progenitor cell" in the present invention refers to a progenitor cell that can be differentiated into any mature retinal cell of a photoreceptor, a horizontal cell, a bipolar cell, an amacrine cell, and a retinal ganglion cell.

On the other hand, the photoreceptor precursor, horizontal precursor cell, bipolar precursor cell, amacrine precursor cell, and retinal ganglion precursor cell are precursor cells determined to differentiate into a photoreceptor, a horizontal cell, a bipolar cell, an amacrine cell, and a retinal ganglion cell, respectively.

The "retinal pigment epithelium" in the present invention means an epithelial cell present on the outer side of the neural retinal tissue in the retina of a living body. Whether or not a retinal pigment epithelium can be easily confirmed by those of ordinary skill in the art by, for example, expression of a cell marker (RPE65 (pigment epithelium), Mitf (pigment epithelium), etc.), the presence of melanin granule, characteristic polygonal cell form and so on.

The medium to be used in the present invention can be prepared from a medium used for culture of animal cell as a basal medium. Examples of the basal medium include BME medium, BGJb medium, CMRL1066 medium, Glasgow MEM medium, Improved MEM Zinc Option medium, IMDM medium, Medium199 medium, Eagle MEM medium, αMEM medium, DMEM medium, ham medium, RPMI1640 medium, Fischer's medium, and mixed medium thereof, and the medium is not particularly limited as long as it can be used for culturing animal cells.

The "serum-free medium" in the present invention means a medium free of unadjusted or unpurified serum. A medium containing purified blood-derived components and animal tissue-derived components (e.g., growth factor) is considered a serum-free medium unless unadjusted or unpurified serum is contained therein.

The medium is not particularly limited as long as it is as defined above. However, to avoid complicated preparation, a serum-free medium (GMEM or DMEM, 0.1 mM 2-mercaptoethanol, 0.1 mM non-essential amino acid Mix, 1 mM sodium pyruvate) added with an appropriate amount (e.g., 1-20%) of commercially available KSR can be used as the serum-free medium.

In addition, the serum-free medium may contain a serum replacement. The serum replacement can appropriately contain, for example, albumin, transferrin, fatty acid, collagen precursor, trace element, 2-mercaptoethanol or 3' thiolglycerol, an equivalent thereof and so on. Such serum replacement can be prepared by, for example, the method described in WO98/30679. In addition, to perform the method of the present invention more conveniently, the serum replacement can be a commercially available product. Examples of such commercially available serum replacement include Chemically-defined Lipid concentrated (manufactured by Gibco), and Glutamax (manufactured by Gibco).

The serum-free medium to be used for floating culture can contain fatty acid or lipid, amino acid (e.g., non-essential amino acid), vitamin, growth factor, cytokine, antioxidant, 2-mercaptoethanol, pyruvic acid, buffering agent, inorganic salts and so on.

The "serum-containing medium" in the present invention means a medium containing unadjusted or unpurified serum. The medium is not particularly limited as long as it is as defined above. In addition, the serum-containing medium can contain fatty acid or lipid, amino acid (e.g., non-essential amino acid), vitamin, growth factor, cytokine, antioxidant, 2-mercaptoethanol, pyruvic acid, buffering agent, inorganic salts and so on.

The "floating culture" in the present invention means cultivating under conditions prohibiting adhesion of cell or cell mass to a cell culture vessel material and so on.

The cell culture vessel to be used in floating culture is not particularly limited as long as it enables "floating culture", and those of ordinary skill in the art can appropriately determine same. Examples of such cell culture vessel include flask, tissue culture flask, dish, petri dish, tissue culture dish, multidish, microplate, microwell plate, micropore, multiplate, multiwell plate, chamber slide, schale, tube, tray, culture bag, and roller bottle. Since these cell culture vessels are used for floating culture, they are preferably cell non-adhesive. As a cell non-adhesive vessel, one having its surface not artificially treated to improve cell adhesiveness (e.g., coating treatment with extracellular matrix, etc.) and so on can be used.

The "primates" in the present invention mean mammals belonging to primate. Examples of the primates include Strepsirrhini such as lemur, loris, and Tsubai, and Haplorhini such as monkey, anthropoid ape, and human.

<Production Method of Retinal Tissue>

The first aspect of the present invention is a method for producing a retinal tissue, comprising the following steps (1) to (3):

(1) a first step of subjecting pluripotent stem cells to floating culture in a serum-free medium containing a substance inhibiting the Wnt signal pathway to form an aggregate of pluripotent stem cells, (2) a second step of subjecting the aggregate formed in the first step to floating culture in a serum-free medium containing a basement membrane preparation, and (3) a third step of subjecting the aggregate cultured in the second step to floating culture in a serum-containing medium.

(1) First Step

The first step of subjecting pluripotent stem cells to floating culture in a serum-free medium containing a substance inhibiting the Wnt signal pathway to form an aggregate of pluripotent stem cells is explained.

A substance inhibiting the Wnt signal pathway is not particularly limited as long as it can suppress signal transduction mediated by Wnt. Examples of the substance inhibiting the Wnt signal pathway include Dkk1, Cerberus protein, Wnt receptor inhibitor, soluble-type Wnt receptor, Wnt antibody, casein kinase inhibitor, dominant negative Wnt protein, CKI-7 (N-(2-aminoethyl)-5-chloro-isoquinoline-8-sulfonamide), D4476 (4-{4-(2,3-dihydrobenzo[1,4]dioxin-6-yl)-5-pyridin-2-yl-1H-imidazol-2-yl}benzamide), IWR-1-endo (IWR1e), IWP-2 and so on.

The concentration of the substance inhibiting the Wnt signal pathway to be used in the present invention only needs to be a concentration at which aggregates of pluripotent stem cells are formed. For example, a common substance inhibiting the Wnt signal pathway such as IWR1e is added at a concentration of about 0.1 μM to 100 μM, preferably about 1 μM to 10 μM, more preferably about 3 μM.

A substance inhibiting the Wnt signal pathway may be added to serum-free medium before the start of the floating culture, or added to a serum-free medium within several days from the start of the floating culture (e.g., within 5 days). Preferably, a substance inhibiting the Wnt signal pathway is added to a serum-free medium within 5 days, more preferably within 3 days, from the start of the floating culture, most preferably simultaneously with the start of the floating culture. In addition, floating culture is performed up to day 18, more preferably day 12, from the start of the floating culture with the addition of a substance inhibiting the Wnt signal pathway.

The culture conditions such as culture temperature, and $CO_2$ concentration in the first step can be appropriately determined. While the culture temperature is not particularly limited, it is, for example, about 30 to 40° C., preferably about 37° C. The $CO_2$ concentration is, for example, about 1 to 10%, preferably about 5%.

The "aggregate" in the present invention refers to a mass of the cells dispersed in the medium but gathered to form same. The "aggregate" in the present invention includes an aggregate formed by the cells dispersed at the start of the floating culture and an aggregate already formed at the start of the floating culture.

When cells are aggregated to form cell aggregates and the aggregates are subjected to floating culture, to "form aggregate" means to "rapidly aggregate a given number of dispersed stem cells" to form qualitatively homogeneous cell aggregates.

Examples of the experimental operation to form an aggregate include a method involving keeping cells in a small space by using a plate with small wells (96 well plate), micropore and so on, a method involving aggregating cells by centrifugation for a short time using a small centrifugation tube, and so on.

The concentration of the pluripotent stem cells in the first step can be determined as appropriate by those of ordinary skill in the art to form aggregates of pluripotent stem cells more uniformly and efficiently. The concentration of the pluripotent stem cells when forming aggregates is not particularly limited as long as it permits formation of uniform aggregates of stem cells. For example, when human ES cells are subjected to floating culture using a 96 well microwell plate, a liquid prepared to about $1\times10^3$ to about $5\times10^4$ cells, preferably about $3\times10^3$ to about $3\times10^4$ cells, more preferably about $5\times10^3$ to about $2\times10^4$ cells, most preferably about $9\times10^3$ cells, per well is added, and the plate is left standing to form aggregates.

The time of floating culture necessary for forming aggregates can be determined as appropriate according to the pluripotent stem cell to be used, as long as the cells can be aggregated rapidly. To form uniform aggregates, it is desirably as short as possible. For example, in the case of human ES cells, aggregates are desirably formed preferably within 24 hr, more preferably within 12 hr. The time for aggregate formation can be appropriately adjusted by those of ordinary skill in the art by controlling the tools for aggregating the cells, centrifugation conditions and so on.

Those of ordinary skill in the art can determine whether aggregates of pluripotent stem cells have been formed, based on the size and cell number of aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

(2) Second Step

The second step of subjecting the aggregate formed in the first step to floating culture in a serum-free medium containing a basement membrane preparation is explained.

The "basement membrane preparation" refers to one containing basement membrane-constituting components having a function to control cell form, differentiation, growth, motility, expression of function and so on which are similar to those of epithelial cell, when intended cells capable of forming a basement membrane are plated thereon and cultured. Here, the "basement membrane constituting component" refers to an extracellular matrix molecule in the form of a thin membrane present between epithelial cell layer and interstitial cell layer and so on in animal tissues. A basement membrane preparation can be produced by, for example, removing cells capable of forming a basement membrane, which adhere onto a support via a basement membrane, with a solution capable of dissolving the lipid of the cells, an alkali solution and so on. Examples of preferable basement membrane preparation include products commercially available as basement membrane components (e.g., Matrigel (hereinafter, sometimes referred to as Matrigel)), and extracellular matrix molecules known as basement membrane components (e.g., laminin, type IV collagen, heparan sulfate proteoglycan, entactin and so on).

Matrigel is a product prepared from a basement membrane derived from Engelbreth Holm Swarn (EHS) mouse sarcoma. The main component of Matrigel is type IV collagen, laminin, heparan sulfate proteoglycan, and entactin. In addition to these, TGF-β, fibroblast growth factor (FGF), tissue plasminogen activator, and a growth factor naturally produced by EHS tumor are contained. The "growth factor reduced product" of Matrigel has a lower growth factor concentration than common Matrigel, and the standard concentration thereof is <0.5 ng/ml for EGF, <0.2 ng/ml for NGF, <5 pg/ml for PDGF, 5 ng/ml for IGF-1, and 1.7 ng/ml for TGF-β. In the method of the present invention, "growth factor reduced product" is preferably used.

While the concentration of the basement membrane preparation to be added to a serum-free medium for the floating culture in the second step is not particularly limited as long as the epithelial structure of the neural tissue (for example, retinal tissue) is stably maintained, for example, it is preferably $\frac{1}{20}$ to $\frac{1}{200}$ volume, more preferably about $\frac{1}{100}$ volume, of the culture medium when Martigel is used. While basement membrane preparation may already have been added to the medium when the culture of stem cell is started, it is preferably added to the serum-free medium within 5 days, more preferably within 2 days, from the start of the floating culture.

As the serum-free medium to be used in the second step, the serum-free medium used in the first step may be directly used, or may be replaced with a fresh serum-free medium. When the serum-free medium used in the first step is directly used for this step, the "basement membrane preparation" can be added to the medium.

The serum-free medium used for the floating culture in the first step and the second step is not particularly limited as long as it is as defined above. However, to avoid complicated preparation, a serum-free medium (GMEM or DMEM, 0.1 mM 2-mercaptoethanol, 0.1 mM non-essential amino acid Mix, 1 mM sodium pyruvate) added with an appropriate amount of commercially available KSR (Knockout Serum Replacement) is preferably used as the serum-free medium. The amount of KSR to be added to the serum-free medium is not particularly limited and, for example, it is generally 1 to 20%, preferably 2 to 20%, in the case of human ES cells.

The culture conditions such as culture temperature, and $CO_2$ concentration in the second step can be appropriately determined. While the culture temperature is not particularly limited, it is, for example, about 30 to 40° C., preferably about 37° C. The $CO_2$ concentration is, for example, about 1 to 10%, preferably about 5%.

(3) Third Step

The third step of subjecting the aggregate cultured in the second step to floating culture in a serum-containing medium is explained.

As the serum-containing medium to be used in the third step, may be used the serum-free medium used in the culture of the second step to which a serum is directly added, or one replaced with a fresh serum-containing medium.

As the serum to be added to a medium in the third step, for example, mammalian serum such as bovine serum, calf serum, fetal calf serum, horse serum, colt serum, fetal horse serum, rabbit serum, leveret serum, fetal rabbit serum, and human serum, and so on can be used.

The serum is added on or after day 7, more preferably on or after day 9, most preferably on day 12, from the start of the floating culture. The concentration of the serum to be added is about 1 to 30%, preferably about 3 to 20%, more preferably about 10%.

The serum-containing medium to be used in the third step is not particularly limited as long as it is as defined above. The above-mentioned serum-free medium (GMEM or DMEM, 0.1 mM 2-mercaptoethanol, 0.1 mM non-essential amino acid Mix, 1 mM sodium pyruvate) to which a serum is added is preferably used.

As such serum-containing medium, one to which an appropriate amount of commercially available KSR (Knock-out Serum Replacement) is added may also be used.

In the third step, the production efficiency of retinal tissue can be increased by adding a substance acting on the Shh signal pathway in addition to the serum.

The substance acting on the Shh signal pathway is not particularly limited as long as it can enhance signal transduction mediated by Shh. Examples of the substance acting on the Shh signal pathway include proteins belonging to the Hedgehog family (e.g., Shh), Shh receptor, Shh receptor agonist, Purmorphamine, SAG and so on.

The concentration of the substance acting on the Shh signal pathway used in this step is, for example, in the case of common substance acting on the Shh signal pathway such as SAG, about 0.1 nM to 10 μM, preferably about 10 nM to 1 μM, more preferably about 100 nM.

The thus-produced retinal tissue is present to cover the surface of the aggregate. Whether a retinal tissue is produced by the production method of the present invention can be confirmed by such immunostaining method as described in the following (4).

It is also possible to physically cut out the retinal tissue present on the surface of aggregates with tweezers and so on. In this case, since a neural tissue other than a retinal tissue may be formed on the surface of each aggregate, a part of the neural tissue cut out from the aggregate is severed and confirmed by such immunostaining method as described in (4), whereby the tissue is confirmed to be a retinal tissue.

(4) Confirmation Method of Retinal Tissue

A retinal tissue can be produced through the above-mentioned first step to the third step. Moreover, production of a retinal tissue through the first step to the third step can be confirmed by the following method.

The aggregate cultured in the third step is subjected to floating culture in a serum-containing medium. Examples of the cell culture vessel to be used for floating culture include those mentioned above. The culture conditions such as culture temperature, $CO_2$ concentration, and $O_2$ concentration of the floating culture can be appropriately determined. While the culture temperature is not particularly limited, it is, for example, about 30 to 40° C., preferably about 37° C. The $CO_2$ concentration is, for example, about 1 to 10%, preferably about 5%. The $O_2$ concentration is, for example, 20 to 70%, preferably 20 to 60%, more preferably 30 to 50%.

While the culture period in this step is not particularly limited, it is generally not less than 48 hr, preferably not less than 7 days.

The retinal tissue can be confirmed by, after completion of the floating culture, fixing the aggregates with a fixative such as para-formaldehyde solution, preparing a frozen section, and confirming formation of a layer structure by an immunostaining method and so on. Since respective layers of a retinal tissue are composed of different retinal progenitor cells (photoreceptor, horizontal cell, bipolar cell, amacrine cell, retinal ganglion cell), formation of a layer structure can be confirmed by an immunostaining method using antibodies against the aforementioned markers expressed in these cells.

<Production Method of Optic-Cup-Like Structure>

The second aspect of the present invention is a production method of an optic-cup-like structure, comprising a step of subjecting the retinal tissue obtained by the above-mentioned <production method of retinal tissue> to floating culture in a serum-free medium or a serum-containing medium each containing a substance acting on the Shh signal pathway and a substance acting on the Wnt signal pathway. As the retinal tissue obtained in the above-mentioned <production method of retinal tissue>, an aggregate containing the retinal tissue cultured in the third step of the above-mentioned <production method of retinal tissue> can be used. As the embodiment of the second invention, a method for producing an optic-cup-like structure, comprising the following steps (1) to (4) can be mentioned:

(1) a first step of subjecting pluripotent stem cells to floating culture in a serum-free medium containing a substance inhibiting the Wnt signal pathway to form an aggregate of pluripotent stem cells, (2) a second step of subjecting the aggregate formed in the first step to floating culture in a serum-free medium containing a basement membrane preparation, (3) a third step of subjecting the aggregate cultured in the second step to floating culture in a serum-containing medium, and (4) a fourth step of subjecting the aggregate cultured in the third step to floating culture in a serum-free medium or serum-containing medium each containing a substance acting on the Shh signal pathway and a substance acting on the Wnt signal pathway.

Here, the substance acting on the Shh signal pathway is not particularly limited as long as it can enhance signal transduction mediated by Shh. Examples of the substance acting on the Shh signal pathway include proteins belonging to Hedgehog family (e.g., Shh), Shh receptor, Shh receptor agonist, Purmorphamine, SAG and so on.

The concentration of the substance acting on the Shh signal pathway to be used in the second aspect of the present invention is, for example, in the case of common substance acting on the Shh signal pathway such as SAG, about 0.1 nM to 10 μM, preferably about 10 nM to 1 μM, more preferably about 100 nM.

Examples of the substance acting on the Wnt signal pathway include protein belonging to Wnt family, Wnt receptor, Wnt receptor agonist, GSKβ (inhibitor (e.g., 6-Bromoindirubin-3'-oxime (BIO), CHIR99021, Kenpaullone) and so on.

The concentration of the substance acting on the Wnt signal pathway to be used in the second aspect of the present invention is, for example, in the case of common substance acting on the Wnt signal pathway such as CHIR99021, about 0.1 μM to 100 μM, preferably about 1 μM to 30 μM, more preferably about 3 μM.

The substance acting on the Shh signal pathway and the substance acting on the Wnt signal pathway are added on or after day 12 and on or before day 25, preferably on or after day 15 and on or before day 18, from the start of the floating culture. In this case, a medium free of the substance inhibiting the Wnt signal pathway added in the aggregate formation step is preferably used.

An optic-cup-like structure is produced in the form of a protrusion from an aggregate on or after day 18 from the start of the floating culture. Whether it is an optic-cup-like structure can be confirmed by those of ordinary skill in the art by observation with a microscope, a magnifying glass and so on.

The thus-produced optic-cup-like structure is formed in a two-layer structure of outer layer and inner layer. Since retinal pigment epitheliua are present in the outer layer and the retinal progenitor cells are present in the inner layer, the retinal progenitor cell and the retinal pigment epithelium can be observed by, for example, preparing a frozen section of the optic-cup-like structure and performing immunostaining.

Furthermore, since the optic-cup-like structure produced by the method of the present invention is formed in the form of a protrusion from an aggregate, it is also possible to obtain a highly pure retinal progenitor cell by physically and morphologically cutting out the protrusion from the aggregate, followed by applying the resulting optic-cup-like structures to a dispersion treatment (e.g., trypsin/EDTA treatment) and FACS sorting. The method for cutting out the optic-cup-like structure is not particularly limited, and it can be cut out easily from an aggregate of stem cells using fine tweezers and so on.

<Production Method of Retinal Layer-Specific Neural Cell>

The third aspect of the present invention is a method of producing a retinal layer-specific neural cell, comprising bringing a retinal progenitor cell contained in a retinal tissue derived from a primate pluripotent stem cell into contact with a substance inhibiting the Notch signal pathway. According to the method of the present invention, a retinal layer-specific neural cell can be produced from a retinal progenitor cell.

(Production Method of Primate Pluripotent Stem Cell-Derived Retinal Tissue)

The "primate pluripotent stem cell-derived retinal tissue" used in the production method of the retinal layer-specific neural cell is explained.

As a primate pluripotent stem cell-derived retinal tissue, for example, the retinal tissue obtained by the above-mentioned <production method of retinal tissue>, or the retinal tissue produced from the optic-cup-like structure obtained by the above-mentioned <production method of optic-cup-like structure> can be used.

In the latter case, the retinal tissue can be produced by subjecting the optic-cup-like structure formed in the fourth step of the above-mentioned <production method of optic-cup-like structure> to a further floating culture.

Since an optic-cup-like structure is formed in the form of a protrusion from an aggregate, as mentioned above, a highly pure retinal tissue can be obtained by physically and morphologically cutting out the protrusion from the aggregate, followed by separation and culturing. The method for cutting out the optic-cup-like structure is not particularly limited, and it can be cut out easily from an aggregate of stem cells using fine tweezers and so on.

The retinal tissue and the optic-cup-like structure produced as mentioned above contain retinal progenitor cells, and retinal layer-specific neural cells can be produced from retinal progenitor cells by bringing the aforementioned retinal progenitor cells into contact with a substance inhibiting the Notch signal pathway.

<Substance Inhibiting the Notch Signal Pathway>

Next, the substance inhibiting Notch signal pathway used in the production method of the retinal layer-specific neural cell is explained.

The substance inhibiting Notch signal pathway is not particularly limited as long as it can inhibit signal transduction mediated by Notch. Examples of the substance inhibiting the Notch signal pathway include Notch antibody, Notch receptor antagonist, ADAM inhibitor, gamma secretase inhibitor and so on.

Examples of the Gamma Secretase Inhibitor Include N-[N-(3,5-difluorophenacetyl)-L-alanyl]-S-phenylglycine t-butyl ester (DAPT)

The concentration of the gamma secretase inhibitor is not particularly limited as long as it can enhance differentiation of retinal progenitor cell into photoreceptor precursor cell or photoreceptor. The concentration is, for example, in the case of common gamma secretase inhibitors, about 0.1 to 1000 μM, preferably about 1 to 100 μM, more preferably about 10 μM.

The gamma secretase inhibitor is added on or after day 15 and on or before day 200 from the start of the floating culture of primate pluripotent stem cells, for the retinal tissues produced from primate pluripotent stem cells. Preferably, a gamma secretase inhibitor is added to the medium on or after day 20 and on or before day 150, more preferably on or after day 25 and on or before day 100, of differentiation induction.

The period of the adhesion culture in the presence of the gamma secretase inhibitor can be a length which allow more efficient production of the photoreceptor precursor cell or photoreceptor. The length of such period can be, for example, about 3 days or more, preferably about 5 to 100 days, more preferably about 7 to 30 days.

(Confirmation Method of Retinal Layer-Specific Neural Cell)

A method for confirming a retinal layer-specific neural cell produced as mentioned above is explained by referring to the case where the retinal layer-specific neural cell is a photoreceptor, a photoreceptor precursor, or a ganglion cell.

Whether the produced retinal layer-specific neural cell is a photoreceptor precursor cell can be confirmed by a known method, for example, expression of a photoreceptor precursor cell marker. Examples of the photoreceptor precursor cell marker include Crx.

Photoreceptor contains rod cell and cone cell. Whether the produced cell is a photoreceptor can be confirmed by a method known per se, for example, expression of a photoreceptor marker. Examples of the photoreceptor marker include rhodopsin (rod cell), red/green opsin (cone cell), blue opsin (cone cell) recoverin (rod cell, cone cell) and so on.

In addition, whether the produced retinal layer-specific neural cell is a ganglion cell can be confirmed by a known method, for example, expression of ganglion cell marker. Examples of the ganglion cell marker include Brn3.

After completion of the adhesion culture, photoreceptor precursor cell or photoreceptor can be isolated from the retinal tissue. Such isolation can be performed by a method known per se (cell sorter etc.) and using an antibody against the surface marker of a photoreceptor precursor cell or photoreceptor and so on. In addition, after completion of the culture, a ganglion cell can be isolated from the retinal tissue. Such isolation can be performed by a method known per se (cell sorter etc.) and using an antibody against the surface marker of a ganglion cell and so on. Alternatively, by using, as a pluripotent stem cell, a cell wherein a labeled gene (e.g., fluorescent protein such as GFP) has been knocked in-frame in a gene encoding a marker (e.g., Crx) of a photoreceptor precursor cell or a marker (e.g., recoverin) of a photoreceptor or a marker (Brn3) of a ganglion cell, each cell can be isolated by a method known per se (cell sorter etc.) using the expression of the label gene as an indicator.

<Production Method of Retinal Pigment Epithelium>

The fourth aspect of the present invention is a production method of a retinal pigment epithelium, comprising a step of subjecting the retinal tissue obtained by the above-mentioned <production method of retinal tissue> to floating culture in a serum-free medium or a serum-containing medium each containing a substance acting on the Wnt signal pathway (but not containing a substance acting on the Sonic hedgehog signal pathway). As the retinal tissue obtained in the above-mentioned <production method of retinal tissue>, an aggregate containing the retinal tissue cultured in the third step of the above-mentioned <production method of retinal tissue> can be used. As the embodiment of the fourth invention, a method of producing a retinal pigment epithelium, comprising the following steps (1) to (4) can be mentioned:

(1) a first step of subjecting pluripotent stem cells to floating culture in a serum-free medium containing a substance inhibiting the Wnt signal pathway to form an aggregate of pluripotent stem cells, (2) a second step of subjecting the aggregate formed in the first step to floating culture in a serum-free medium containing a basement membrane preparation, (3) a third step of subjecting the aggregate cultured in the second step to floating culture in a serum-containing medium, and (4) a fourth step of subjecting the aggregate cultured in the third step to floating culture in a serum-free medium or serum-containing medium each containing a substance acting on the Wnt signal pathway, wherein the aforementioned serum-free medium and serum-containing medium are free of a substance acting on the Sonic hedgehog signal pathway.

Here, examples of the substance acting on the Wnt signal pathway include proteins belonging to Wnt family, Wnt receptor, Wnt receptor agonist, GSKβ (inhibitor (e.g., 6-Bromoindirubin-3'-oxime (BIO), CHIR99021, Kenpaullone) and so on.

The concentration of the substance acting on the Wnt signal pathway to be used in the fourth aspect of the present invention is, for example, in the case of common substance acting on the Wnt signal pathway such as CHIR99021, about 0.1 μM to 100 μM, preferably about 1 μM to 30 μM, more preferably about 3 μM.

The substance acting on the Wnt signal pathway is added on or after day 12, most preferably on day 15, when, for example, human ES cells are used. In this case, preferably used is a medium free of the substance inhibiting the Wnt signal pathway added in the first step and the substance acting on the Shh signal pathway added in the third step.

In the fourth aspect of the present invention, the retinal tissue or the aggregate containing a retinal tissue, which is obtained by the above-mentioned <production method of retinal tissue>, is preferably cultured in a serum-free medium or a serum-containing medium each containing a substance acting on the Wnt signal pathway and a substance acting on the Activin signal pathway.

The substance acting on the Activin signal pathway is not particularly limited as long as it can enhance signal transduction mediated by Activin. Examples of the substance acting on the Activin signal pathway include proteins belonging to the Activin family (e.g., Activin A, Activin B, Activin C, and Activin AB, etc.), Activin receptor, Activin receptor agonist and so on.

The concentration of the substance acting on the Activin signal pathway to be used in this step is, for example, in the case of common substance acting on the Activin signal pathway such as Recombinant Human/Mouse/Rat Activin A (R&D systems #338-AC), 1 ng/ml to 10 ug/ml, preferably about 10 ng/ml to 1 ug/ml, more preferably about 100 ng/ml.

Since the thus-produced retinal pigment epithelium is present on the surface of aggregates, it can be easily observed by microscopic observation and so on. It is also possible to obtain a highly pure retinal pigment epithelium by subjecting an aggregate containing the retinal pigment epithelium to, for example, a dispersion treatment (e.g., trypsin/EDTA treatment) followed by FACS sorting. It is also possible to physically cut out the retinal pigment epithelium from the aggregates with tweezers and so on, followed by cultivation. The retinal pigment epithelium after dispersion or cutting out can be cultured under adhesion conditions. In the case of adhesion culture, a cell adhesive culture vessel, for example, a culture vessel after a coating treatment with an extracellular matrix etc. (e.g., poly-D-lysine, laminin, fibronectin), is preferably used. The culture conditions of the adhesion culture such as culture temperature, $CO_2$ concentration, and $O_2$ concentration can be easily determined by those of ordinary skill in the art. In this case, culture may be performed in the presence of a serum, a known growth factor, an additive and a chemical substance that promote the growth. Examples of the known growth factor include EGF, FGF and so on. Examples of the additive that promotes the growth include N2 supplement (Invitrogen), B27 supplement (Invitrogen) and so on.

<Use of Retinal Tissue as a Reagent for Evaluating Toxicity or Drug Efficacy>

The retinal tissue, optic-cup-like structure, retinal layer-specific neural cell and retinal pigment epithelium produced by the first to the fourth aspects of the present invention can also be used for screening for a therapeutic drug for a disease due to a disorder of retinal tissue or retina-related cell, or a transplantation material for cell treatment, a material for the study of diseases or a drug discovery material for a therapeutic drug for a cell damage due to other etiology. In addition, they can be utilized for the study, test and so on of such toxicity as phototoxicity in the toxicity and drug efficacy evaluation of chemical substances and so on.

Examples of the disease due to a disorder of retinal tissue or retina-related cell include organic mercury poisoning, chloroquine retinopathy, retinitis pigmentosa, age-related macular degeneration, glaucoma, diabetic retinopathy, neonatal retinopathy, and so on.

<Use of Retinal Tissue, Optic-Cup-Like Structure, Retinal Layer-Specific Neural Cell and Retinal Pigment Epithelium as Biological Materials for Transplantation>

The retinal tissue, optic-cup-like structure, retinal layer-specific neural cell and retinal pigment epithelium produced by the first to the fourth aspects of the present invention can be used as biological materials for transplantation used for supplementing a damaged cell or disordered tissue itself in a cell damage state (e.g., used for transplantation operation) and so on. Examples of the transplantation method include, but are not limited to, the methods described in the below-mentioned Examples.

The production method of the present invention is explained in more detail in the following by referring to Comparative Examples and Examples. The Examples merely show exemplification of the present invention and do not limit the scope of the present invention in any way.

EXAMPLES (Establishment of RAX Knock-In Human ES Cell)

Human ES cell line with GFP knocked-in at the RAX gene locus, which is one of the marker genes of retinal progenitor cell, was produced.

Zinc Finger Nuclease (ZFN) that specifically cleaves RAX gene on genomic DNA of human ES cell line (KhES-1: human ES cell line established by Kyoto University) was purchased from Sigma-Aldrich Co. LLC. Using human ES cells which were dissociated to single cells and according to the electroporation method, ZFN-coding mRNA and a knock-in vector carrying GFP and a neomycin-resistance gene, which is a drug selection gene, were co-transfected, and plated on neomycin resistance mouse fibroblast treated with mitomycin C. From the next day of plating, G418 was added into the medium and drug selection was performed. The colony of the obtained resistant clone was picked up, culture was continued, and knock-in cells were selected by the PCR method and the Southern blot method, whereby a RAX::GFP-knock-in human ES cell line was established.

Comparative Example 1: Production of Retinal Tissue by Using Human ES Cells (Matrigel Addition Conditions)

RAX::GFP knock-in human ES cells (derived from KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5 to 10 ng/ml bFGF was used. The ES cells were dispersed into single cells by using 0.25% trypsin-EDTA (Invitrogen), and floating-cultured in a serum-free medium (100 μl) at 37° C., 5% $CO_2$ to $9×10^{-}3$ cells per well of a non-cell adhesive 96-well culture plate (SUMILON spheroid plate, SUMITOMO BAKELITE CO., LTD.). As the serum-free medium in this case, a serum-free medium obtained by adding 20% KSR, 0.1 mM 2-mercaptoethanol, 1 mM pyruvic acid and 20 μM Y27632 to G-MEM medium was used. During the floating culture, Matrigel in an amount of ¹⁄₁₀₀ per volume was added from day 2 from the start of the floating culture. Thereafter, fluorescence microscopic observation was regularly performed while continuing the floating culture.

Figure 1:
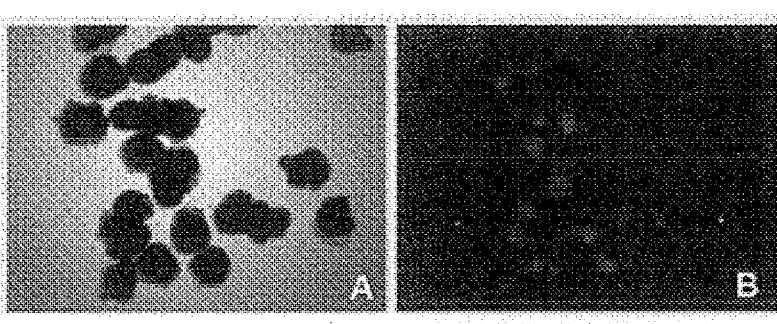
FIG. 1 is a view that shows a bright-field image (A) and a fluorescence image (B) of human pluripotent stem cell-derived aggregates, which were produced by adding Matrigel (hereinafter, sometimes referred to as Matrigel) alone and without adding a substance inhibiting the Wnt signal pathway, on day 25 from the start of the floating culture, a bright-field image (C) and a fluorescence image (D) of human pluripotent stem cell-derived aggregates, which were produced by adding a substance inhibiting the Nodal signal pathway and Matrigel, on day 25 from the start of the floating culture, and a bright-field image (E) and a fluorescence image (F) of human pluripotent stem cell-derived aggregates, which were produced by adding a substance inhibiting the Wnt signal pathway and Matrigel, on day 25 from the start of the floating culture.
Figure 1:
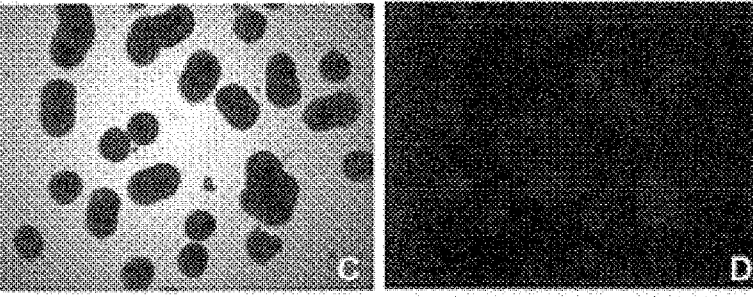
Figure 1:
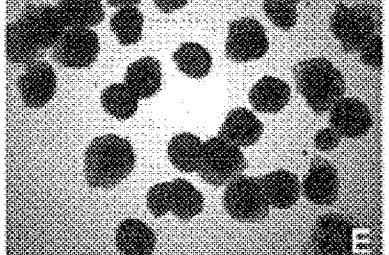
Figure 1:
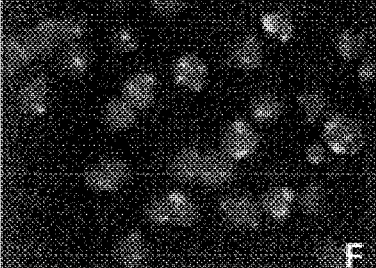

As a result of the fluorescence microscopic observation up to day 25 from the start of the floating culture, GFP expression cells showing induction of the retinal progenitor cells were somewhat found (FIGS. 1A, B).

Comparative Example 2: Production of Retinal Tissue by Using Human ES Cells (Nodal Signal Pathway Inhibitor and Matrigel Addition Conditions)

RAX::GFP knock-in human ES cells (derived from KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5-10 ng/ml bFGF was used. For the production of retinal tissue by floating culture, the ES cells were dissociated into single cells by using 0.25% trypsin-EDTA (Invitrogen), and floating-cultured in a serum-free medium (100 μl) at 37° C., 5% $CO_2$ to $9×10^3$ cells per well of a non-cell adhesive 96-well culture plate (SUMILON spheroid plate, SUMITOMO BAKELITE CO., LTD.). As the serum-free medium in this case, a serum-free medium obtained by adding 20% KSR, 0.1 mM 2-mercaptoethanol, 1 mM pyruvic acid, 20 μM Y27632 and a substance inhibiting the Nodal signal pathway (10 μM SB431542) to G-MEM medium was used. During the floating culture, Matrigel in an amount of ¹⁄₁₀₀ per volume was added from day 2 from the start of the floating culture. Thereafter, the floating culture was continued and fluorescence microscopic observation and confirmation of the proportion of the GFP-expressing cells were performed by FACS on day 18 from the start of the floating culture.

As a result, GFP-expressing cells were somewhat found (FIGS. 1C, D).

Comparative Example 3: Production of Retinal Tissue by Using Human ES Cells (Wnt Signal Pathway Inhibitor and Matrigel Addition Conditions)

RAX::GFP knock-in human ES cells (derived from KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5 to 10 ng/ml bFGF was used. For the production of retinal tissue by floating culture, the ES cells were dispersed into single cells by using 0.25% trypsin-EDTA (Invitrogen), and floating-cultured in a serum-free medium (100 μl) at 37° C., 5% $CO_2$ to $9×10^3$ cells per well of a non-cell adhesive 96-well culture plate (SUMILON spheroid plate, SUMITOMO BAKELITE CO., LTD.). As the serum-free medium in this case, a serum-free medium obtained by adding 20% KSR, 0.1 mM 2-mercaptoethanol, 1 mM pyruvic acid, 20 μM Y27632 and a substance inhibiting the Wnt signal pathway (3 μM IWR1e) to G-MEM medium was used. During the floating culture, Matrigel in an amount of ¹⁄₁₀₀ per volume was added from day 2 from the start of the floating culture. Thereafter, the floating culture was continued and fluorescence microscopic observation and confirmation of the proportion of the GFP-expressing cells were performed by FACS on day 18 from the start of the floating culture.

As a result, the GFP-expressing cells clearly increased (FIGS. 1E, F) as compared to Comparative Examples 1 and 2.

Example 1: Production of Retinal Tissue by Using Human ES Cells (Wnt Signal Pathway Inhibitor and Matrigel, Serum Addition Conditions)

RAX::GFP knock-in human ES cells (derived from KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5 to 10 ng/ml bFGF was used. For the production of retinal tissue by floating culture, the ES cells were dispersed into single cells by using 0.25% trypsin-EDTA (Invitrogen), and floating-cultured in a serum-free medium (100 μl) at 37° C., 5% $CO_2$ to $9×10^3$ cells per well of a non-cell adhesive 96-well culture plate (SUMILON spheroid plate, SUMITOMO BAKELITE CO., LTD.). As the serum-free medium in this case, a serum-free medium obtained by adding 20% KSR, 0.1 mM 2-mercaptoethanol, 1 mM pyruvic acid, 20 μM Y27632 and a substance inhibiting the Wnt signal pathway (3 μM IWR1e) to G-MEM medium was used. During the floating culture, Matrigel in an amount of ¹⁄₁₀₀ per volume was added from day 2 from the start of the floating culture. Furthermore, a fetal calf serum in a ¹⁄₁₀ amount per volume was added on day 12 from the start of the floating culture. Thereafter, the floating culture was continued and fluorescence microscopic observation and confirmation of the proportion of the GFP-expressing cells were performed by FACS on day 18 from the start of the floating culture.

Simultaneously, an experiment was also performed under the conditions of Comparative Example 3, which were free of the addition of a serum.

Figure 3:
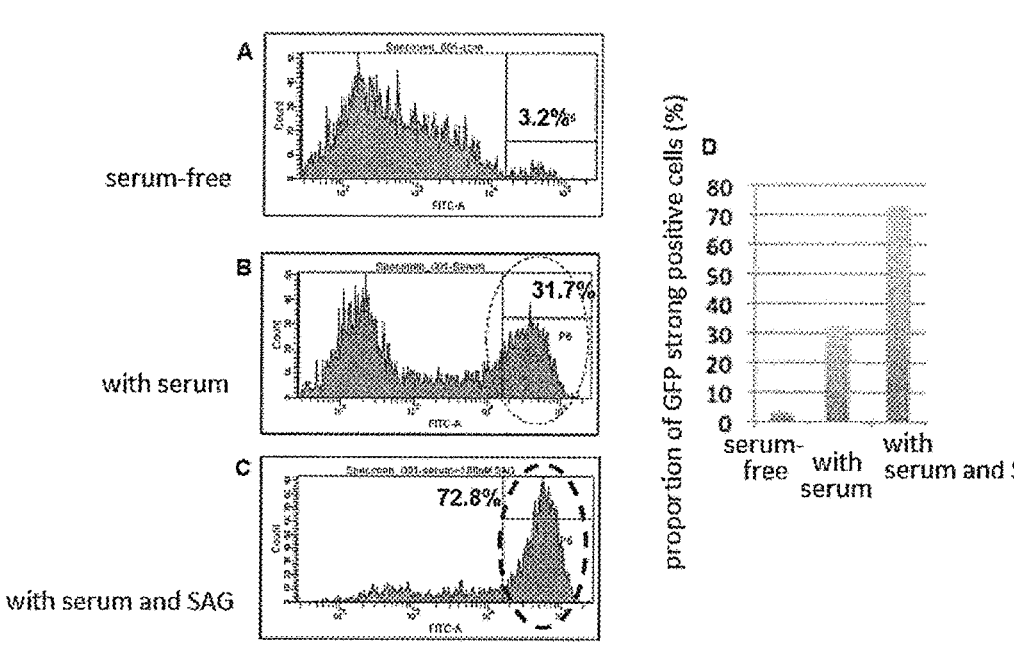
FIG. 3 shows FACS histograms (A) of GFP-expressing cell constituting aggregates on day 18 from the start of the floating culture, which were produced by floating culture of human pluripotent stem cells by adding a substance inhibiting the Wnt signal pathway, floating culture thereof in the presence of Matrigel and further floating culture thereof in the absence of fetal calf serum, FACS histograms (B) of GFP-expressing cell constituting aggregates on day 18 from the start of the floating culture, which were produced by floating culture of human pluripotent stem cells by adding a substance inhibiting the Wnt signal pathway, floating culture thereof in the presence of Matrigel and further floating culture thereof in the presence of fetal calf serum, FACS histograms (C) of GFP-expressing cell constituting aggregates on day 18 from the start of the floating culture, which were produced by floating culture of human pluripotent stem cells by adding a substance inhibiting the Wnt signal pathway, floating culture thereof in the presence of Matrigel and further floating culture thereof in the presence of fetal calf serum and a substance inhibiting the Shh signal pathway, and a graph (D) showing the proportion of GFP strong positive cells, which are retinal progenitor cells.

While the proportion of the GFP-expressing cells under the conditions of Comparative Example 3 was 3.2% (FIGS. 2A, B, FIG. 3A), many GFP-expressing cells emerged under the conditions with the addition of a serum (FIGS. 2C, D). The proportion of the GFP-positive cells was over 30% in the analysis by FACS (FIG. 3B).

Example 2: Production of Retinal Tissue by Using Human ES Cells (Conditions with Addition of Wnt Signal Pathway Inhibitor and Matrigel, Serum and a Substance Acting on the Shh Signal)

RAX::GFP knock-in human ES cells (derived from KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5 to 10 ng/ml bFGF was used. For the production of retinal tissue by floating culture, the ES cells were dispersed into single cells by using 0.25% trypsin-EDTA (Invitrogen), and floating-cultured in a serum-free medium (100 µl) at 37° C., 5% $CO_2$ to $9\times10^3$ cells per well of a non-cell adhesive 96-well culture plate (SUMILON spheroid plate, SUMITOMO BAKELITE CO., LTD.). As the serum-free medium in this case, a serum-free medium obtained by adding 20% KSR, 0.1 mM 2-mercaptoethanol, 1 mM pyruvic acid, 20 µM Y27632 and a substance inhibiting the Wnt signal pathway (3 µM IWR1e) to G-MEM medium was used. During the floating culture, Matrigel in an amount of $\frac{1}{100}$ per volume was added from day 2 from the start of the floating culture. A fetal calf serum in an amount of $\frac{1}{10}$ per volume and a substance acting on the Shh signal pathway (100 nM SAG) were added on day 12 from the start of the floating culture. The proportion of the GFP-expressing cells was measured by FACS on day 18 from the start of the floating culture.

When a substance acting on the Shh signal pathway was added simultaneously with a serum, a very high number of GFP-expressing cells emerged (FIGS. 2E, F). From the analysis using FACS, the proportion of the GFP-expressing cells was found to have reached not less than 70%.

It was found that, as compared to Comparative Example 3, the proportion of the GFP-expressing cells increased to about 10-fold under the conditions of Example 1 wherein a serum was added, and further, the proportion of the GFP-expressing cells increased to about 24-fold under the conditions of Example 2 wherein a serum and a substance acting on the Shh signal pathway were simultaneously added (FIG. 3D).

Example 3: Confirmation of Retinal Tissue Formation (Method)

Formation of retinal tissue was confirmed with the aggregates having GFP-expressing cells, which were produced in Examples 2 and 3. Using a serum-containing medium obtained by adding N2 supplement, 10% (v/v) fetal calf serum and 0.5 µM retinoic acid to DMEM/F12 medium, floating culture was performed under the conditions of 40% $O_2$ from day 18 from the start of the floating culture. Thereafter, the aggregated mass was fixed with 4% para-formaldehyde solution, a frozen section was prepared, and the tissue structure was confirmed by the immunostaining method.

Figure 4:
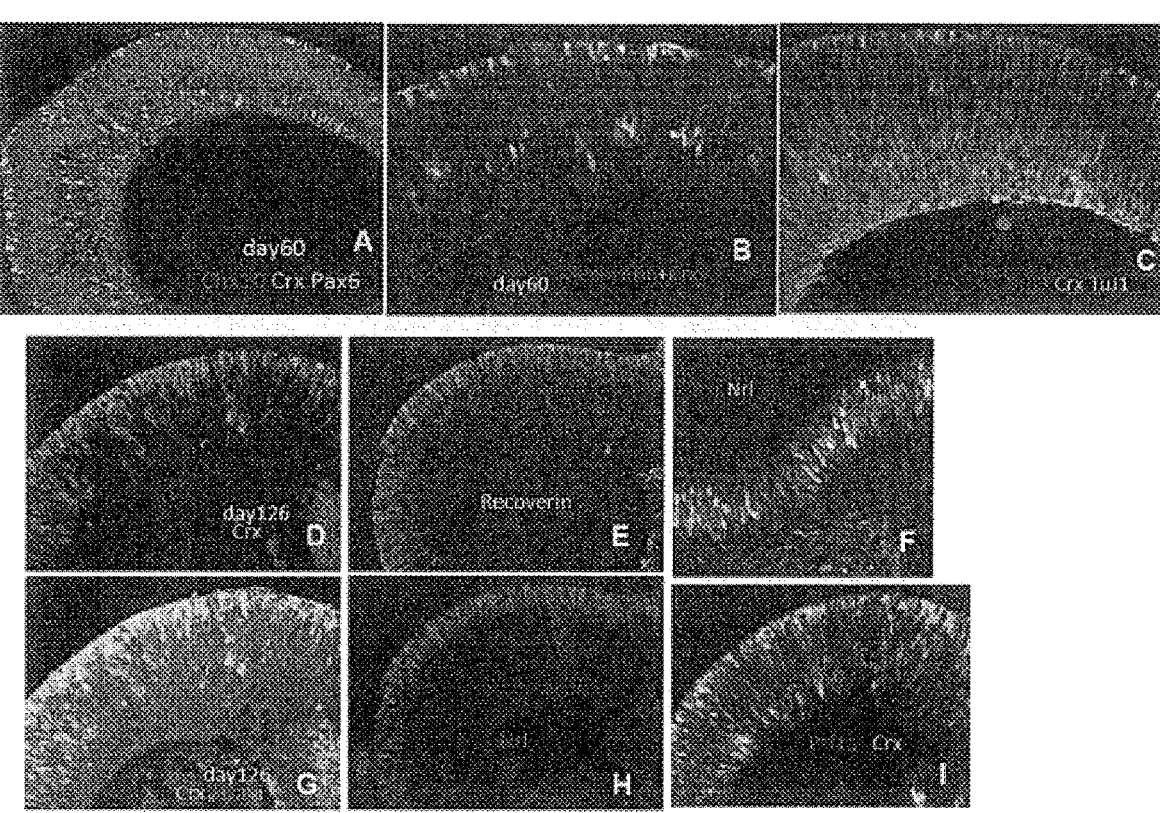
FIG. 4 is a view that shows the results of immunostaining of retinal tissues (A, B, C) on day 60 from the start of the floating culture and retinal tissues (D, E, F, G, H, I) on day 126 from the start of the floating culture, which were produced by the production method of retinal tissue of the present invention.

As a result, it was revealed on day 60 from the start of the floating culture that Brn3 and TuJ1-positive ganglion cells in the lowermost layer, Crx and Recoverin-positive photoreceptor-precursor cells in the outermost layer and intermediate layer, and interneuron progenitor cells such as Chx10-positive bipolar cells between the Brn3-positive cells in the outermost layer and the Brn3-positive cells in the lowermost layer were arranged in layers in an orderly manner (FIGS. 4A, B, C). Furthermore, when the floating culture was continued until day 126, Crx and Recoverin-positive photoreceptor-precursor cells were accumulated in the outermost layer, and the cells expressing Nrl that is specifically expressed in rod cells and the cells expressing Rxr-gamma that is specifically expressed in cone cells were observed. In addition, the cells expressing Ptfla, which is a precursor cell marker of horizontal cell and amacrine cell, were observed in the intermediate layer (FIGS. 4D, E, F, G, H, I). From these results, it has been shown that a retinal tissue can be produced at high efficiency from human ES cells.

Example 4: Transplantation into Eye of Retinal Tissue Produced from Human ES Cell After incision of the sclera of an eyeball, an injection needle was inserted from the sclera incision into the vitreous to lower the intraocular pressure. An intraocular perfusion fluid was injected from the sclera incision into subretinal space with a cell transplantation needle to artificially form a shallow retinal detachment state. The retinal tissue is transplanted with a cell transplantation needle or a cell sheet transplantation device into the space formed.

Example 5: Production of Optic-Cup-Like Structure at High Efficiency Using Human ES Cell (Method)

Using RAX::GFP knock-in human ES cells, an optic-cup-like structure was produced.

RAX::GFP knock-in human ES cells (derived from KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5 to 10 ng/ml bFGF was used. For the formation of aggregate by floating culture, the ES cells were dispersed into single cells by using 0.25% trypsin-EDTA (Invitrogen), suspended in a serum-free medium (100 µl) to $9\times10^3$ cells per well of a non-cell adhesive 96-well culture plate (SUMILON spheroid plate, SUMITOMO BAKELITE CO., LTD.) to allow for rapid formation of aggregates, and floating cultured at 37° C., 5% $CO_2$. As the serum-free medium in this case, a serum-free medium obtained by adding 20% KSR, 0.1 mM 2-mercaptoethanol, 1 mM pyruvic acid, 20 µM Y27632 and a substance inhibiting the Wnt signal pathway (3 µM IWR1e) to G-MEM medium was used. During the floating culture, Matrigel in an amount of $\frac{1}{100}$ per volume was added from day 2 from the start of the floating culture. The floating aggregate was transferred to a serum-free medium without a substance inhibiting the Wnt signal pathway on day 12 from the start of the floating culture, fetal calf serum in an amount of $\frac{1}{10}$ per volume was added and the aggregate was cultured. Furthermore, the floating culture was performed in a serumcontaining medium containing a substance acting on the Wnt signal pathway (3 μM CHIR99021) and a substance acting on the Shh signal pathway (100 nM SAG) from day 15.

(Results)

Figure 5:
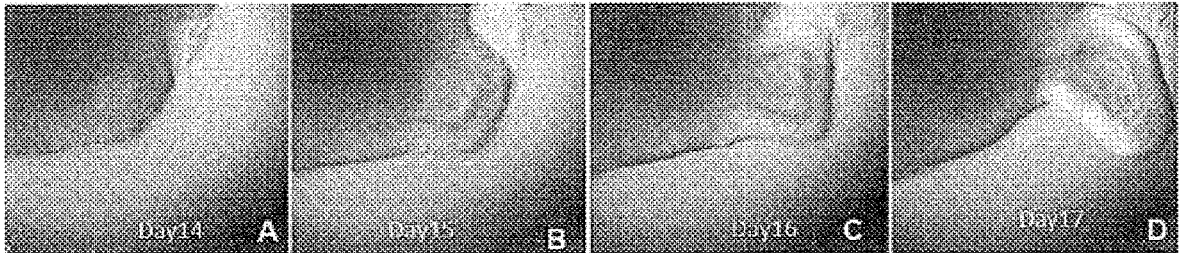
FIG. 5 is a view that shows images of an overlap of a bright-field and a fluorescence image of the same part of an aggregate on day 14 (A), day 15 (B), day 16 (C), day 17 (D) from the start of the floating culture by the production method of an optic-cup-like structure of the present invention.
Figure 6:
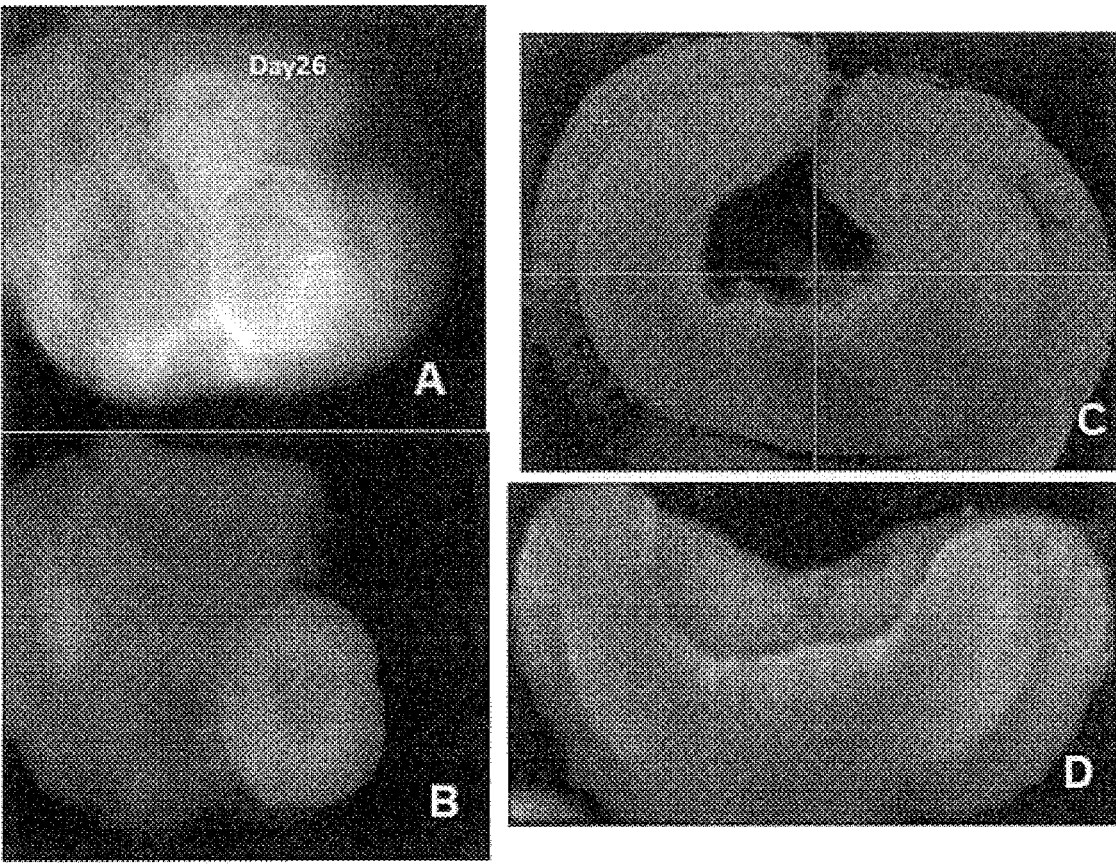
FIG. 6 is a view that shows a bright-field image (A) and a fluorescence image (B) by microscopic observation, and a two-photon microscope observation image (C) and a 3D reconstitution image (D) obtained from a two-photon microscopic observation image, of a floating cultured aggregate on days 24 to 26 from the start of the floating culture by the production method of an optic-cup-like structure of the present invention.
Figures 7, 8:
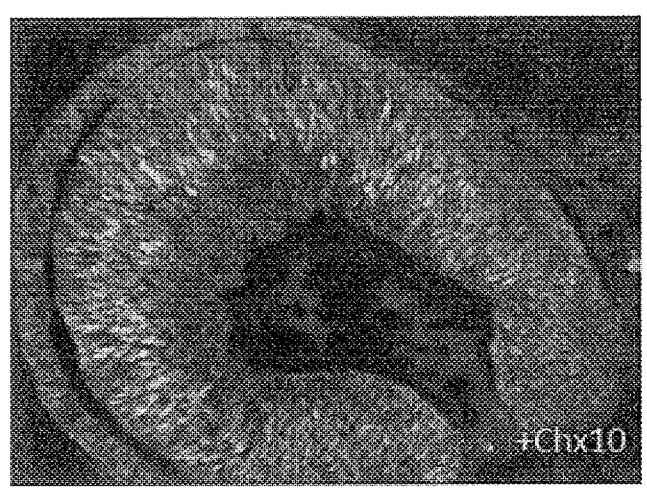
FIG. 7 is a view that shows the results of immunostaining of a frozen section of an optic-cup-like structure produced by floating culture by the production method of an optic-cup-like structure of the present invention, with an anti-Mitf antibody and an anti-Chx10 antibody.
FIG. 8 is a view that shows a fluorescence microscope (A) in the case of floating culture until day 41 from the start of the floating culture, the start of the floating culture under the conditions without addition of 10 μM DAPT, a fluorescence microscope (B) in the case of floating culture until day 41 from the start of the floating culture under the conditions with addition of DAPT, photograph of a frozen section immunostained with an anti-Recoverin antibody (C) or with an anti-Brn3 antibody (E) in the case of floating culture until day 43 from the start of the floating culture under the conditions without addition of 10 μM DAPT, and photograph of frozen section immunostained with an anti-Recoverin antibody (D) or with an anti-Brn3 antibody (F) in the case of floating culture until day 43 of differentiation induction under the conditions with addition of DAPT, each of which using a Crx::GFP knock-in human ES cell-derived retinal tissue on day 29 from the start of the floating culture.

When produced by the above-mentioned method, a GFP-positive cell population showing expression of RAX emerged in a part of the aggregate around day 14 from the start of the floating culture (FIG. 5A), which then raised toward the outer side of the aggregate (FIGS. 5B, C). When the floating culture was continued, a clear protrusion was formed (FIG. 5D). Furthermore, when the floating culture was continued, a clear optic-cup-like structure was formed on the aggregate composed of the GFP-positive cells (retinal progenitor cells) (FIG. 6). This optic-cup-like structure could be clearly recognized simply by microscopic observation of the aggregate (FIG. 6A). When the optic-cup-like structure formed on the aggregate was observed in depth by a two-photon microscope to find that it had a two-layer structure of the outside and the inside (FIGS. 6C, D). A frozen section of the optic-cup-like structure was prepared and immunostained. As a result, a layer of retinal pigment epithelia expressing Mitf was present on the outside, and Chx10-positive neural retinal progenitor cells were present in the inside thereof (FIG. 7).

Example 6: Transplantation into Eye of Optic-Cup-Like Structure Produced from Human ES Cell After incision of the sclera of an eyeball, an injection needle was inserted from the sclera incision into the vitreous to lower the intraocular pressure. An intraocular perfusion fluid was injected from the sclera incision into subretinal space with a cell transplantation needle to artificially form a shallow retinal detachment state. The cultured optic-cup-like structure is transplanted with a cell transplantation needle or a cell sheet transplantation device into the space formed.

Example 7: Treatment of Human ES Cell-Derived Retinal Tissue with a Substance Acting on the Notch Signal CrX::GFP knock-in human ES cells (derived from KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5 to 10 ng/ml bFGF was used. The ES cells were dispersed into single cells by using 0.25% trypsin-EDTA (Invitrogen), and floating-cultured in a serum-free medium (100 μl) at 37° C., 5% $CO_2$ to 9×10^3 cells per well of a non-cell adhesive 96-well culture plate (SUMILON spheroid plate, SUMITOMO BAKELITE CO., LTD.). As the serum-free medium in this case, a serum-free medium obtained by adding 20% KSR, 0.1 mM 2-mercaptoethanol, 1 mM pyruvic acid, 20 μM Y27632 and a substance inhibiting the Wnt signal pathway (3 μM IWR1e) to G-MEM medium was used. Matrigel was added in an amount of ⅟₁₀₀ per volume from day 2 of the floating culture and floating culture was performed. Fetal calf serum in an amount of ⅟₁₀ per volume and a substance acting on the Shh signal pathway (100 nM SAG) were added on day 12 of floating culture and the floating culture was performed to produce a retinal tissue. A substance acting on the Notch signal (10 μM DAPT (gamma secretase activity inhibitor))

was added to the retinal tissue on day 29 from the start of the floating culture, observed with a fluorescence microscope on day 41 from the start of the floating culture (day 12 after the addition), and fixed with 4% para-formaldehyde on day 43 from the start of the floating culture (day 14 after the addition), and a frozen section was prepared. The prepared frozen section was immunostained for Recoverin, which is one of the marker genes of photoreceptor, and Brn3, which is one of the marker genes of ganglion cells, and the results were compared between the presence and absence of DAPT-addition.

As a result, the GFP-expressing cells markedly increased when DAPT was added (FIG. 8B), as compared to when DAPT was not added (FIG. 8A). In addition, from the results of immunostaining of the frozen section, it was revealed that Recoverin-positive cells increased 3- to 5-fold when DAPT was added (FIGS. 8C, D).

These results show a marked increase in the photoreceptors. In addition, it was found from the results of immunostaining of Brn3 that the ganglion cells also increased by the addition of DAPT (FIGS. 8E, F).

Example 8: Treatment of Human ES Cell-Derived Retinal Tissue after Freeze-Thawing with a Substance Acting on the Notch Signal RAX::GFP knock-in human ES cells (derived from KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5 to 10 ng/ml bFGF was used. For the production of retinal tissue by floating culture, the ES cells were dispersed into single cells by using 0.25% trypsin-EDTA (Invitrogen), and floating-cultured in a serum-free medium (100 μl) at 37° C., 5% $CO_2$ to 9×10^3 cells per well of a non-cell adhesive 96-well culture plate (SUMILON spheroid plate, SUMITOMO BAKELITE CO., LTD.). As the serum-free medium in this case, a serum-free medium obtained by adding 20% KSR, 0.1 mM 2-mercaptoethanol, 1 mM pyruvic acid, 20 μM Y27632 and a substance inhibiting the Wnt signal pathway (3 μM IWR1e) to G-MEM medium was used. A serum-free medium added with Matrigel in an amount of ⅟₁₀₀ per volume was used from day 2 from the start of the floating culture. Matrigel was added in an amount of ⅟₁₀₀ per volume from day 2 of the floating culture and floating culture was performed. Fetal calf serum in an amount of ⅟₁₀ per volume and a substance acting on the Shh signal pathway (100 nM SAG) were added on day 12 from the start of the floating culture and the floating culture was performed to produce a retinal tissue. The produced retinal tissue on day 33 from the start of the floating culture was freeze-thawed, and a Notch signal action inhibitory substance (10 μM DAPT) was added to the retinal tissue on day 38 from the start of the floating culture. The tissue was observed with a fluorescence microscope on day 49 from the start of the floating culture (day 11 after the addition), and fixed with 4% para-formaldehyde, and a frozen section was prepared. The prepared frozen section was immunostained for Recoverin, which is one of the marker genes of photoreceptor, and Brn3, which is one of the marker genes of ganglion cells, and the results were compared between the presence and absence of DAPT-addition.

As a result, the GFP-expressing cells were markedly produced when DAPT was added (FIG. 9B), as compared to when DAPT was not added (FIG. 9A). In addition, from the results of immunostaining of the frozen section, it was revealed that Recoverin-positive cells were produced about 5-fold when DAPT was added (FIGS. 9C, D). These results show a marked production of the photoreceptors. In addition, it was found from the results of immunostaining of Brn3 that the ganglion cells were also produced by the addition of DAPT (FIGS. 9E, F).

Example 9: Transplantation into Eye of Retinal Layer-Specific Neural Cell Produced from Human ES Cell After incision of the sclera of an eyeball, an injection needle was inserted from the sclera incision into the vitreous to lower the intraocular pressure. An intraocular perfusion fluid was injected from the sclera incision into subretinal space with a cell transplantation needle to artificially form a shallow retinal detachment state. The retinal layer-specific neural cell is transplanted with a cell transplantation needle or a cell sheet transplantation device into the space formed.

Example 10: Production of Retinal Pigment Epithelium at High Efficiency Using Human ES Cell (Method)

Human ES cells (KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement; Invitrogen), 0.1 mM 2-mercaptoethanol, 1 mM pyruvic acid, and 5 to 10 ng/ml bFGF was used. For the formation of retinal tissue by floating culture, the ES cells were dispersed into single cells by using 0.25% trypsin-EDTA (Invitrogen), suspended in a serum-free medium (100 µl) to $9 \times 10^3$ cells per well of a non-cell adhesive 96-well culture plate (SUMILON spheroid plate, SUMITOMO BAKELITE CO., LTD.) to allow for rapid formation of aggregates, and floating cultured at 37° C., 5% $CO_2$. As the serum-free medium in this case, a serum-free medium obtained by adding 20% KSR, 0.1 mM 2-mercaptoethanol, 1 mM pyruvic acid, 20 µM Y27632 and a substance inhibiting the Wnt signal pathway (3 µM IWR1e) to G-MEM medium was used. Matrigel was added in an amount of ¹⁄₁₀₀ per volume from day 2 of the floating culture and floating culture was performed. The aggregate was transferred to a serum-free medium without containing a substance inhibiting the Wnt signal pathway on day 12 from the start of the floating culture, fetal calf serum in an amount of ¹⁄₁₀ per volume was added and cultured. The floating culture was performed in a medium containing a substance acting on the Wnt signal pathway (3 µM CHIR99021) from day 15.

(Results)

When produced by the above-mentioned method, a retinal pigment epithelium population emerged on almost all surfaces of the aggregates (FIG. 10).

Example 11: Production of Retinal Pigment Epithelium Using Human ES Cell (Method)

Human ES cells (KhES-1) were cultured according to the methods described in "Ueno, M. et al. PNAS 2006", "Watanabe, K. et al. Nat Biotech 2007" and used for the experiment. As the medium, DMEM/F12 medium (Invitrogen) added with 20% KSR (Knockout Serum Replacement;

Invitrogen), 0.1 mM 2-mercaptoethanol, 1 mM pyruvic acid, and 5 to 10 ng/ml bFGF was used. For the formation of retinal tissue by floating culture, the ES cells were dispersed into single cells by using 0.25% trypsin-EDTA (Invitrogen), suspended in a serum-free medium (100 µl) to $9 \times 10^3$ cells per well of a non-cell adhesive 96-well culture plate (SUMILON spheroid plate, SUMITOMO BAKELITE CO., LTD.) to allow for rapid formation of aggregates, and floating cultured at 37° C., 5% $CO_2$. As the serum-free medium in this case, a serum-free medium obtained by adding 20% KSR, 0.1 mM 2-mercaptoethanol, 1 mM pyruvic acid, 20 µM Y27632 and a substance inhibiting the Wnt signal pathway (3 µM IWR1e) to G-MEM medium was used. During the floating culture, Matrigel in an amount of ¹⁄₁₀₀ per volume was added from day 2 from the start of the floating culture. The aggregate was transferred to a serum-free medium without containing a substance inhibiting the Wnt signal pathway on day 12 from the start of the floating culture, fetal calf serum in an amount of ¹⁄₁₀ per volume was added and cultured. The floating culture was performed in a medium containing a substance acting on the Wnt signal pathway (3 µM CHIR99021) and a substance acting on the Activin signal pathway (Recombinant Human/Mouse/Rat Activin A (R&D systems #338-AC) 100 ng/ml) from day 15.

(Results)

When produced by the above-mentioned method, retinal pigment epithelia taking on black color emerged on surfaces of almost all the aggregates. Furthermore, almost all the surfaces of the aggregates were covered with retinal pigment epithelia (FIG. 11), and retinal pigment epithelia were produced at surprisingly high efficiency.

Example 12: Transplantation into Eye of Retinal Pigment Epithelium Produced from Human ES Cell After incision of the sclera of an eyeball, an injection needle was inserted from the sclera incision into the vitreous to lower the intraocular pressure. An intraocular perfusion fluid was injected from the sclera incision into subretinal space with a cell transplantation needle to artificially form a shallow retinal detachment state. The retinal pigment epithelium is transplanted with a cell transplantation needle or a cell sheet transplantation device into the space formed.

INDUSTRIAL APPLICABILITY

According to the present invention, a retinal tissue, optic-cup-like structure, retinal layer-specific neural cell or retinal pigment epithelium can be produced at high efficiency. The production method of the present invention is highly useful since it efficiently produces a cell group (such as photoreceptor and optic nerve) constituting a retinal tissue, for the purpose of toxicity or drug efficacy evaluation of a chemical substance, etc., a cell treatment and so on, as well as efficiently produces a retinal tissue to be a "tissue material" to be used for tests and treatments for the purpose of application to a toxicity or drug efficacy evaluation using a retinal tissue with a tissue structure, and to a transplantation material for a retinal tissue transplantation treatment.

This application is based on patent application Nos. 2011-258209, 2011-258210, 2011-258211, 2011-258212, 2012-043080, 2012-043081, 2012-043082 and 2012-043083 filed in Japan, the contents of which are incorporated in full herein.

The invention claimed is:

1. An artificial cell aggregate consisting of a human retinal tissue, with Brn3 and TuJ1-positive ganglion cells in the lowermost layer of the retinal tissue, Crx and Recoverin-positive photoreceptor-precursor cells in the outermost layer and intermediate layer of the retinal tissue, and interneuron progenitor cells between the outermost layer and the lowermost layer of the retinal tissue, wherein the lowermost layer, intermediate layer, and outermost layer form a layered structure, and Crx and Recoverin-positive photoreceptor-precursor cells are accumulated in the outermost layer.

2. The cell aggregate according to claim 1, wherein the interneuron progenitor cells comprise Chx10-positive bipolar cells.

3. The cell aggregate according to claim 1, which comprises no less than 70% of RAX-positive cells.

4. The cell aggregate according to claim 1, which comprises Nrl-positive cells and Rxr-gamma-positive cells.

5. The cell aggregate according to claim 1, which comprises rod cells and cone cells.

6. The cell aggregate according to claim 1, which comprises Ptfla-positive cells.

7. The cell aggregate according to claim 1, which comprises horizontal cells or amacrine cells.

8. The cell aggregate according to claim 1, which are differentiated in vitro from pluripotent stem cells.

9. A retinal tissue which is cut out from the cell aggregate according to claim 1.

10. A cell culture comprising the cell aggregate according to claim 1 and a medium.

11. A transplant comprising the cell aggregate according to claim 1 and a medium.

12. A transplant comprising the retinal tissue according to claim 9 and a medium.

\*    \*    \*    \*    \*